(12) United States Patent
Silverman et al.

(10) Patent No.: US 12,320,816 B2
(45) Date of Patent: Jun. 3, 2025

(54) ASSAY DEVICE FOR DIAGNOSIS OF OPEN-GLOBE OCULAR INJURIES

(71) Applicant: Triton Systems, Inc., Chelmsford, MA (US)

(72) Inventors: Andrew Silverman, Cambridge, MA (US); Dmitry Shvartsman, Sudbury, MA (US); Jason Lasser, Andover, MA (US)

(73) Assignee: Triton Systems, Inc., Chelmsford, MA (US)

(*) Notice: Subject to any disclaimer, the term of this patent is extended or adjusted under 35 U.S.C. 154(b) by 0 days.

(21) Appl. No.: 18/882,314

(22) Filed: Sep. 11, 2024

(65) Prior Publication Data

US 2025/0085298 A1    Mar. 13, 2025

Related U.S. Application Data

(60) Provisional application No. 63/581,811, filed on Sep. 11, 2023.

(51) Int. Cl.
| | | |
|---|---|---|
| G01N 33/53 | (2006.01) | |
| G01N 33/543 | (2006.01) | |
| G01N 33/68 | (2006.01) | |

(52) U.S. Cl.
CPC ... G01N 33/6893 (2013.01); G01N 33/54388 (2021.08); *G01N 2800/16* (2013.01)

(58) Field of Classification Search
CPC ......... G01N 33/6893; G01N 33/54388; G01N 2800/16
See application file for complete search history.

(56) References Cited

FOREIGN PATENT DOCUMENTS

| EP | 3981887 | * | 4/2022 | .......... G01N 33/574 |
| WO | WO2007089731 | * | 1/2007 | ............. A61K 31/56 |

OTHER PUBLICATIONS

Millipore Guide ((2008, retrieved from URL:www.millipore.com/publications.nsf/a73664f9f981af8c852569b9005b4eee/348ee7096d93729b85256bf40066a40d/$FILE/tb500en00.pdf).*
Elisa Alpha Crystallin A (MyBiosource 2006, retrieved from https://www.mybiosource.com/human-elisa-kits/alpha-crystallin-a-chain-cryaa/7211785).*
Pluckthun—in The Pharmacology of Monoclonal Antibodies, vol. 113, Rosenburg and Moore eds., Springer-Verlag, New York, pp. 269-315 (1994).
Huse et al., Science 246:1275-1281, 1989.
Winter and Harris, Immunol. Today 14:243-246, 1993.
Ward et al., Nature 341:544-546, 1989.
Harlow & Lane Antibodies: A laboratory manual (Cold Spring Harbor Laboratory Press, 1999).
Hilyard et al., Protein Engineering: A practical approach (IRL Press 1992).
Borrebaeck, Antibody Engineering, 2d ed. (Oxford University Press 1995).

* cited by examiner

*Primary Examiner* — Carmencita M Belei
(74) *Attorney, Agent, or Firm* — Caldwell Intellectual Property Law

(57) ABSTRACT

Methods, kits, and devices for detecting open-globe eye injuries are described. A device including a target recognition element specific for intraocular fluid, appropriate for use in the field is described. A method for detecting an open-globe eye injury by detecting proteins found in intraocular fluid is also described. A device may include a soft absorbent swab for sample collection, a lateral flow assay device, and a blood filter to improve device performance.

8 Claims, 23 Drawing Sheets

Specification includes a Sequence Listing.

700 ⤵

705
Receiving, using a sample receiver, a fluid sample.

710
Binding, using a target recognition element specific to intraocular fluid in fluidic communication with the sample receiver, to a target analyte.

715
Signaling, using a signal producing molecule, the binding of the target recognition element specific to intraocular fluid with the target analyte.

MAB1301 – Heavy Chain

----CDR1----> <---CDR2--> <---CDR3----

[illegible sequence]

MAB1301 – Light Chain

----CDR1----> <---CDR2--> <---CDR3----

[illegible sequence]

MAB1601 – Heavy Chain

----CDR1----> <---CDR2--> <---CDR3----

[illegible sequence]

MAB1601 – Light Chain

----CDR1----> <---CDR2--> <---CDR3----

[illegible sequence]

FIG. 9

| | | Reagent Conditions | | Sample Conditions | | | | | | |
|---|---|---|---|---|---|---|---|---|---|---|
| | Test No. | Conjugate Ab Loading (uL) | T-line Ab Concentration (mg/mL) | Sample Aqueous Humor (uL) | Sample Vitreous Humor (uL) | Sample Aspirin Stock (1 mg/mL) (uL) | Sample Lidocaine Stock (Saturated) (uL) | Sample Human Whole Blood (uL) | Sample PBS (uL) | Sample Total Volume (uL) |
| Blood | 1 | 8 | 1 | 0 | 0 | 0 | 0 | 3 | 7 | 10 |
| | 2 | 8 | 2 | 0 | 0 | 0 | 0 | 3 | 7 | 10 |
| | 3 | 8 | 4 | 0 | 0 | 0 | 0 | 3 | 7 | 10 |
| AH/VH + Blood | 4 | 8 | 1 | 4 | 1 | 0 | 0 | 3 | 2 | 10 |
| | 5 | 8 | 2 | 4 | 1 | 0 | 0 | 3 | 2 | 10 |
| | 6 | 8 | 4 | 4 | 1 | 0 | 0 | 3 | 2 | 10 |
| Blood + Analgesics | 7 | 8 | 1 | 0 | 0 | 1 | 1 | 3 | 5 | 10 |
| | 8 | 8 | 2 | 0 | 0 | 1 | 1 | 3 | 5 | 10 |
| | 9 | 8 | 4 | 0 | 0 | 1 | 1 | 3 | 5 | 10 |
| AH/VH + Blood + Analgesics | 10 | 8 | 1 | 4 | 1 | 1 | 1 | 3 | 0 | 10 |
| | 11 | 8 | 2 | 4 | 1 | 1 | 1 | 3 | 0 | 10 |
| | 12 | 8 | 4 | 4 | 1 | 1 | 1 | 3 | 0 | 10 |

Negative Controls: Positive Test Line Expected

| Arm | Injury Size | Injury Depth | Injury Location | Confounder | Eyes (Rabbits) | Time points |
|---|---|---|---|---|---|---|
| 1 | 3 mm Laceration | Surface | AC Limbus | None | 3 (left) | 15 mins, 8hrs, 24hrs |
| 2 | 3 mm Laceration | Surface | AC Limbus | Blood | 3 (left) | 15 mins, 8hrs, 24hrs |
| 3 | 3 mm Laceration | Full-thickness | AC Limbus | None | 3 (left) + 1 (right)* | 15 mins, 8hrs, 24hrs |
| 4 | 3 mm Laceration | Full-thickness | AC Limbus | Blood | 3 + 1* 3 (left) + 1 (right)* | 15 mins, 8hrs, 24hrs |
| 5 | 1 mm puncture | Full-thickness | AC Limbus | None | 3 + 1*3 (left) + 1 (right)* | 15 mins, 8hrs, 24hrs |
| 6 | 1 mm puncture | Full-thickness | AC Limbus | Blood | 3 + 1*3 (left) + 1 (right)* | 15 mins, 8hrs, 24hrs |
| 7 | 3 mm Laceration | Full-thickness | PC | None | 3 + 1*3 (left) + 1 (right)* | 15 mins, 8hrs, 24hrs |
| 8 | 3 mm Laceration | Full-thickness | PC | Blood | 3 + 1*3 (left) + 1 (right)* | 15 mins, 8hrs, 24hrs |
| 9 | 1 mm puncture | Full-thickness | PC | None | 3 + 1*3 (left) + 1 (right)* | 15 mins, 8hrs, 24hrs |
| 10 | 1 mm puncture | Full-thickness | PC | Blood | 3 + 1*3 (left) + 1 (right)* | 15 mins, 8hrs, 24hrs |

* only one eye injured per rabbit; measurement of contralateral uninjured eye will used as a control.

FIG. 12

ASSAY DEVICE FOR DIAGNOSIS OF OPEN-GLOBE OCULAR INJURIES

CROSS-REFERENCE TO RELATED APPLICATIONS

This application claims the benefit of priority of U.S. Provisional Patent Application Ser. No. 63/581,811, filed on Sep. 11, 2023, and titled "ASSAY DEVICE FOR DIAGNOSIS OF OPEN-GLOBE OCULAR INJURIES," which is incorporated by reference herein in its entirety.

STATEMENT OF GOVERNMENT INTEREST

This invention was made with Government support under Contracts No. WSIXWH-20-C-0027 awarded by the Defense Health Agency of the Department of Defense. The Government has certain rights in this invention.

REFERENCE TO SEQUENCE LISTING

This specification includes a sequence listing submitted herewith, which includes the file entitled 1678-001USU1.xml having the following size: 26,812 bytes which was created Oct. 2, 2024, the contents of which are incorporated by reference herein.

FIELD OF THE INVENTION

The present invention generally relates to the field of diagnostic technology. In particular, the present invention is directed to an assay device for diagnosis of open-globe ocular injuries.

BACKGROUND

Open-globe injuries are those in which the full thickness of the eye wall is disrupted. Because these injuries allow for the extrusion of the eye's internal contents as well as the introduction of external agents into the eye, open-globe injuries represent an emergency situation for which timely diagnosis and treatment is important for decreasing the chances of infection, visual impairment, or loss of the eye. The incidence rates of ocular trauma requiring hospitalization in the USA are reported to be 40,000 incidents annually.

SUMMARY OF THE DISCLOSURE

When delay in primary repair of open-globe injuries is anticipated, for example because of patient transport, anti-inflammatoires and prophylactic antibiotics should be administered as soon as possible. There is a need for a diagnostic device that better supports care providers that are less skilled in differential diagnosis for ruptured globes. Typically, these providers are initially trained at EMT-B level and are the first to treat injured patients. Patients with eye trauma often guard their injuries and will not readily open their eyes. Additionally, access to the eye is often obstructed by swelling or other interfering factors. This scenario makes optical inspection methods nearly impossible. However, without the ability to detect these wounds, the intervention may not be given in time to save vision. The development of a detection device that is appropriate for this realistic scenario would produce a significant advance in minimizing wound related vision loss.

Furthermore, there is a growing need in clinical procedures to ensure a globe is closed after typical cataract surgery or cornea replacement. Cataract surgery is the most frequently performed ophthalmic surgical procedure in developed countries, and as of 2014 the World Health Organization has estimated that roughly 0.3% of the world population become candidates for cataract surgery each year, with the fraction being higher in more developed countries. Many ophthalmic surgeries require a 24 hour check up to ensure the eye has maintained closure.

The Seidel Test, first described in 1921, is still the current standard of care to assess for a leak of intraocular fluid (e.g., aqueous humor) following globe penetration. The test involves the application of a fluorescein dye to the surface of the eye, followed by visualization with a cobalt blue light; fluorescein normally appears red to orange, but turns green when diluted by aqueous humor emerging from an open-globe injury. Despite this, there are many disadvantages for this test, including opportunities for a false negative result to occur. False negatives can result from small wounds that may close over time, if ocular contents (or external contents) "plug" the opening preventing aqueous outflow, or when additional confounders such as dirt or blood serum are present, which can further dilute or change the colors seen on the eye surface. Furthermore, hypersensitivity to fluorescein dye is a contraindication, and any unnecessary manipulation of the globe is also contraindicated. This test also is typically performed in a darkened or dimly lit room to provide as much contrast as possible for thorough evaluation, and so cannot adequately be performed in the immediate aftermath of an injury.

Additional methods for determining full-thickness eye wall disruption include slit-lamp inspection, which can require significant medical expertise to detect smaller lacerations, CT scan, or ultrasound; ultrasound, however, is generally contraindicated because increasing pressure on a ruptured eye could lead to further extrusion of its contents.

In an aspect, a substrate including: a sample receiver configured to receive a fluid sample; a target recognition element specific to intraocular fluid in fluidic communication with the sample receiver, wherein the target recognition element is configured to bind to a target analyte; and a signal producing molecule configured to signal the binding of the target recognition element specific to intraocular fluid with the target analyte. The substrate further includes a flow path from the sample receiver configured to flow the fluid sample; and wherein one or both of the target recognition element and the signal producing molecule are downstream of the sample receiver on the flow path. The substrate further includes a test element downstream from the target recognition element on the flow path and configured to bind, directly or indirectly, to the target analyte. The substrate further includes a blood filter upstream of the test element on the flow path configured to filter red blood cells from fluid. The substrate further includes a control element downstream from the target recognition element on the flow path, wherein the control element is configured to bind to the target recognition element. The target analyte includes at least a portion of α-crystallin A. The target analyte is at least 90% identical to SEQ ID NO: 1. The target analyte includes at least six consecutive amino acids of SEQ ID NO: 2.

In another aspect, a method of use for a substrate comprising: receiving, using a sample receiver, a fluid sample; binding, using a target recognition element specific to intraocular fluid in fluidic communication with the sample receiver, to a target analyte; and signaling, using a signal producing molecule, the binding of the target recognition element specific to intraocular fluid with the target analyte. The method further includes a flow path from the sample receiver configured to flow the fluid sample; and wherein one or both of the target recognition element and the signal producing molecule are downstream of the sample receiver on the flow path. The method further includes a test element downstream from the target recognition element on the flow path and configured to bind, directly or indirectly, to the target analyte. The method further includes a blood filter upstream of the test element on the flow path configured to filter red blood cells from fluid. The method further includes a control element downstream from the target recognition element on the flow path, The control element is configured to bind to the target recognition element. The target analyte includes at least a portion of α-crystallin A. The target analyte is at least 90% identical to SEQ ID NO: 1. The target analyte includes at least six consecutive amino acids of SEQ ID NO: 2.

In another aspect, a fieldable open-globe eye detection system, including: a sampler tool configured to sample a fluid sample from biological fluids proximal to a patient's eye; a substrate including: a sample receiver configured to receive the fluid sample from the sampler tool; a target recognition element specific to intraocular fluid in fluidic communication with the sample receiver, The target recognition element is configured to bind to a target analyte; a signal producing molecule configured to signal the binding of the target recognition element specific to intraocular fluid with the target analyte; a flow path from the sample receiver configured to flow the fluid sample, wherein one or both of the target recognition element and the signal producing molecule are downstream of the sample receiver on the flow path; a test element downstream from the target recognition element on the flow path and configured to bind, directly or indirectly, to the target analyte; and a control element downstream from the target recognition element on the flow path, wherein the control element is configured to bind to the target recognition element; a casing configured to house the substrate and including a display window configured to permit viewing of one or more of the test element and the control element; and a blood filter configured to filter red blood cells from the fluid sample before the fluid sample reaches the test. The system further includes at least a light configured to illuminate one or more of the display window and the test element. The sampler tool includes one or more of a soft swab, a syringe, and a pinch grip. The sampler tool includes a soft swab having a shape with a point and the system further includes a receptor slot configured to receive the soft swab and provide fluidic communication between the soft swab and the sample receiver of the substrate. The sampler tool further includes a syringe containing a buffer, and the sample receiver is further configured to receive the fluid sample within the buffer, directly or indirectly, from the syringe. The target analyte includes at least a portion of α-crystallin A. The target analyte is at least 90% identical to SEQ ID NO: 1. The target analyte includes at least six consecutive amino acids of SEQ ID NO: 2.

In another aspect, a method of using a fieldable open-globe eye detection system, including: sampling, using a sampler tool, a fluid sample from biological fluids proximal to a patient's eye; receiving, using a sample receiver of a substrate, the fluid sample from the sampler tool; binding, using a target recognition element specific to intraocular fluid in fluidic communication with the sample receiver, to a target analyte; signaling, using a signal producing molecule of the substrate, the binding of the target recognition element specific to intraocular fluid with the target analyte; flowing, using a flow path from the sample receiver, the fluid sample, wherein one or both of the target recognition element and the signal producing molecule are downstream of the sample receiver on the flow path; binding, directly or indirectly, using a test element downstream from the target recognition element on the flow path, to the target analyte; binding, using a control element downstream from the target recognition element on the flow path, to the target recognition element; housing, using a casing, the substrate; permit viewing, using a display window of the casing, of one or more of the test element and the control element; and filtering, using a blood filter, red blood cells from the fluid sample before the fluid sample reaches the test. The method further including illuminating, using at least a light, one or more of the display window and the test element. The sampler tool includes one or more of a soft swab, a syringe, and a pinch grip. The sampler tool includes a soft swab having a shape with a point and the method further includes receiving, using a receptor slot, the soft swab; and providing, using the receptor slot, fluidic communication between the soft swab and the sample receiver of the substrate. The sampler tool further includes a syringe containing a buffer, and the method further includes receiving, using the sample receiver the fluid sample within the buffer, directly or indirectly, from the syringe. The target analyte includes at least a portion of α-crystallin A. The target analyte is at least 90% identical to SEQ ID NO: 1. The target analyte includes at least six consecutive amino acids of SEQ ID NO: 2.

In another aspect, a kit for treating an open-globe eye injury including: a sample receiver configured to receive a fluid sample from biological fluids proximal to a patient's eye; a target recognition element specific to intraocular fluid in fluidic communication with the sample receiver, wherein the target recognition element is configured to bind to a target analyte; a signal producing molecule configured to signal the binding of the target recognition element specific to intraocular fluid with the target analyte; and a colorimetric detection system configured to produce a result associated with open-globe eye injury as a function of the signal producing molecule. The target recognition element includes antibody-binding protein, conjugates, antibody-enzyme label conjugates, antibody-gold nanoparticle conjugates, or any combination thereof. The antibody of the target recognition element includes six CDRs of SEQ ID NO: 8-11 and 13-14. The signal producing molecule includes a gold nanoparticle. The sample receiver includes a sampler tool including a swab attached to a handling element. The sampler tool further includes a running buffer. The colorimetric detection system includes an enzyme-linked immunosorbent assay (ELISA). The ELISA is in a sandwich assay format. The kit further includes a substrate. The kit further includes a blood filter configured to filter red blood cells from the fluid sample.

In another aspect, a method for treating an open-globe eye injury in a subject, including: receiving, using a sample receiver, a fluid sample from biological fluids proximal to a patient's eye; binding, using a target recognition element specific to intraocular fluid in fluidic communication with the sample receiver, to a target analyte; signaling, using a signal producing molecule, the binding of the target recognition element specific to intraocular fluid with the target analyte; producing, using a colorimetric detection system, a result associated with open-globe eye injury as a function of the signal producing molecule; and treating the patient for an open-globe eye injury if the result is positive. The target analyte is at least 90% identical to SEQ ID NO: 1. The target analyte is SEQ ID NO: 1. The target analyte includes at least six consecutive amino acids of SEQ ID NO: 2. The target analyte is SEQ ID NO: 2. The target recognition element includes antibody-binding protein, conjugates, antibody-enzyme label conjugates, antibody-gold nanoparticle conjugates, or any combination thereof. The antibody of the target recognition element includes six CDRs of SEQ ID NO: 8-11 and 13-14. The signal producing molecule includes a gold nanoparticle. The method further includes flowing, using a flow path from the sample receiver, the fluid sample; and wherein one or both of the target recognition element and the signal producing molecule are downstream of the sample receiver on the flow path. The method further includes binding, directly or indirectly, using a test element downstream from the target recognition element on the flow path, to the target analyte.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7 illustrates a method of use for a substrate;

FIG. 9 illustrates sequencing results for complementarity determining regions of MAB1301 (Test Line Ab) and MAB1601 (Conjugate Ab);

FIG. 10 illustrates reagent and sample conditions for analgesic interferent experiment;

FIG. 12 illustrates table summarizing the pre-clinical, diagnostic in vivo validation study administration;

Figure 1:
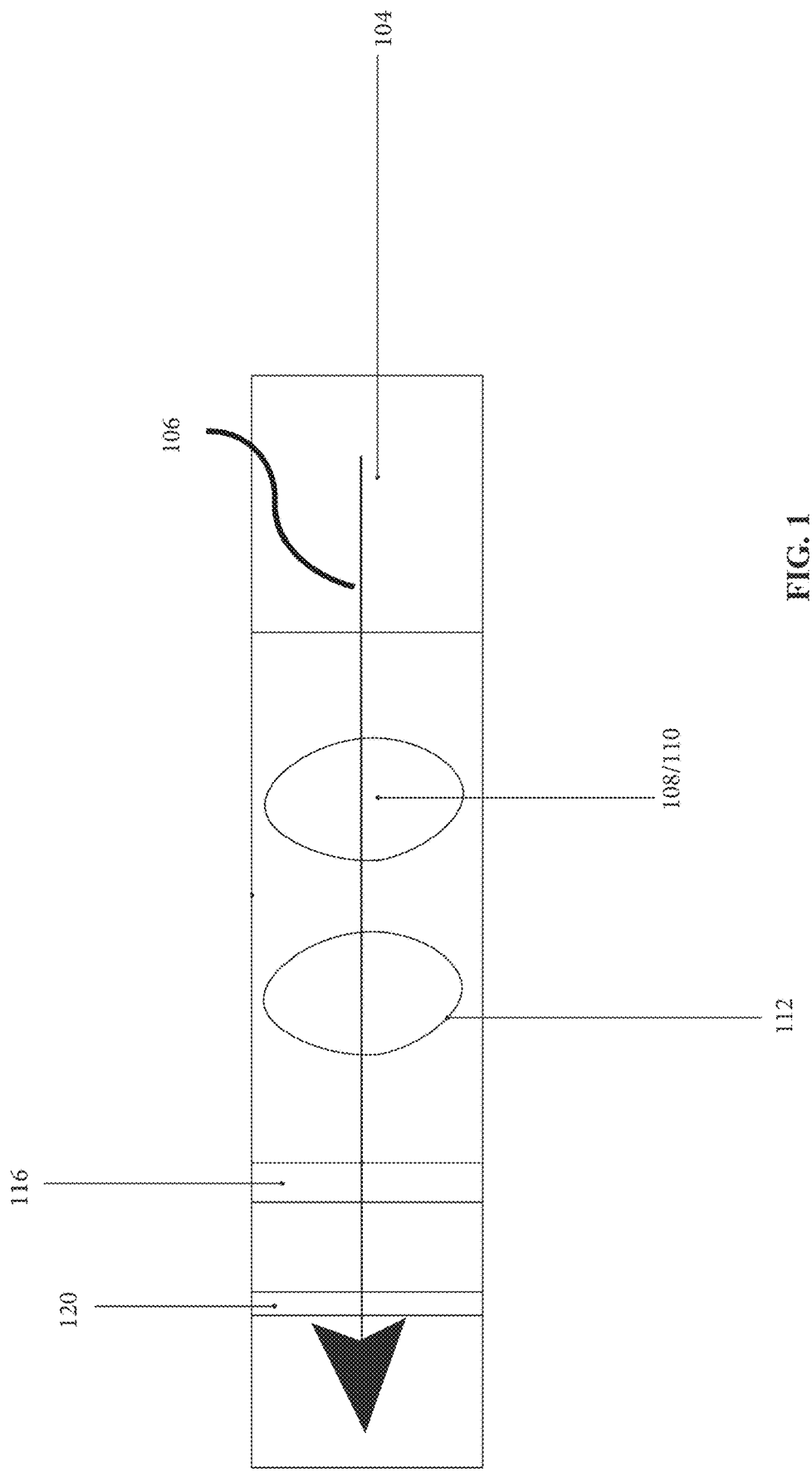
FIG. 1 is a schematic illustration of an exemplary substrate according to some embodiments.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining presence of full thickness ocular globe injury, for example for field use when a patient has sustained an eye injury. Systems described in this disclosure may include a lateral flow assay device.

Aspects of the present disclosure can be used to determine presence of intraocular fluid from animals and humans. Exemplary embodiments illustrating aspects of the present disclosure are described below in the context of several specific examples.

In some embodiments, assay may not require users with extensive expertise or a clinical or laboratory setting to operate, and may be a point-of-care device that may provide an unambiguous result as to presence of an open-globe injury. A fieldable device described in this disclosure may be suitable for use where highly trained medical personnel may be unavailable, and where rapid, accurate test results improve patient outcomes (for example, FIG. 2A). In some cases, device described in this disclosure may be suitable for use in a clinical or laboratory setting. In some cases, lateral flow assay device disclosed herein detects presence of α-crystallin A (CRYAA) (e.g., SEQ ID NO:1). CRYAA is an eye lens protein that is highly abundant in intraocular fluids (aqueous and vitreous humor) but is not found in large concentrations in any potentially confounding extraocular bodily fluids (e.g., tear fluid or blood). In some cases, presence of CRYAA may demonstrate that an eye has suffered an open-globe injury. When an open-globe injury is detected, patient may be referred to urgent medical treatment. In some embodiments, urgent medical treatment includes surgery to repair open-globe injury, reinsertion of eye tissue, restoration of aqueous or vitreous humor, antibiotics, follow-up care, and other appropriate medical interventions.

In some embodiments, a sampling tool may be included. In some cases, sampling tool may contain a soft, pointed, highly absorbent pad, or swab, to allow for more precise sampling of the injured eye surface while minimizing pressure on injured eye wall. In some embodiments, sampling tool may also include a syringe. In some cases, syringe may be filled with a running buffer solution, allowing a user to apply sample to assay and dispense the running buffer in one step. As sample inputs for assay device can contain significant quantities of blood, the assay device may contain a blood filter. In some cases, a blood filter may include an additional layer of material (compared to typical lateral flow assays) which substantially prevents red blood cells from passing the filter, e.g., traveling towards a readout area of the assay device. In some cases, filtering red blood cells may reduce background coloration that can interfere with a user's ability to identify positive and control test lines. In some embodiments, a blood filter is made of fiberglass. A "blood filter," as used herein, is a component or material that selectively removes red blood cells, and optionally other matter, from a sample. In some cases, a blood filter may allow blood plasma and/or other fluid components to pass through, for instance to subsequent areas of a substrate for analysis. In some aspects, blood filter may be incorporated directly into a conjugate pad. In some aspects, blood filter is a separate layer on top of conjugate pad.

If red blood cells are allowed to flow down length of strip of a lateral flow assay device, the red blood cell's color can create a red background that may make result indicators, such as red/pink Test and Control Lines, also referred to as test and control elements as used herein, difficult to see. Blood filter may comprise an additional fiberglass layer that the sample (a presumable mixture of tear fluid, blood, and intraocular fluids, if present) is directly applied to and permits the soluble target analytes to flow into the conjugate pad to interact with the antibody-AuNP conjugates while retaining blood cells. In some cases, additional layer may not be present in typical lateral flow assays, which oftentimes use either a clear bodily fluid (e.g., nasal swab, urine) for a sample, or a heavily diluted sample. A "conjugate pad," as used in this disclosure, is a component that holds one or both of signal-producing molecules and target recognition elements, e.g., labeled antibodies or other detection reagents, which may interact with target analyte as a sample flows through a lateral flow assay system.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As used herein, the term "about" means plus or minus 10% of the numerical value of the number with which it is being used. Therefore, about 50% means in the range of 45%-55%.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 ng/ml refers to groups having 1, 2, or 3 ng/mL. Similarly, a group having 1-5 ng/mL refers to groups having 1, 2, 3, 4, or 5 ng/ml, and so forth.

"Patient" as used in this disclosure is any animal being tested for an open-globe. Patient includes, but is not limited to, humans and non-human vertebrates such as wild, domestic, and farm animals. Patient and "subject" may be used interchangeably within this disclosure. In one aspect, subject may be an animal. In one aspect, subject may be mammal. In one aspect, subject may be a human. In one aspect, subject may be a non-human animal. In one aspect, subject may be a non-human mammal. In one aspect, subject may be a domesticated animal, such as a dog, cat, cow, pig, horse, sheep, or goat. In one aspect, subject may be a companion animal such as a dog or cat. In one aspect, subject may be a livestock animal such as a cow, pig, horse, sheep, or goat. In one aspect, subject may be a zoo animal. In one aspect, subject may be a research animal such as a rodent, dog, or non-human primate. In one aspect, subject may be a non-human transgenic animal such as a transgenic mouse or transgenic pig.

As used in this disclosure, "biomarker" refers to any substance used as an indicator of a biologic state. Thus, a biomarker can be any substance whose detection indicates that an eye globe has sustained an open globe injury, such as, a laceration perforation, microperforation, rupture, blunt trauma, or penetrating injury, causing leakage of intraocular fluid. In evaluating potential eye injury therapies, a biomarker may be used as a surrogate for a symptom such as vision loss, eye deformity, or eye pain. If a treatment alters a biomarker, which has a direct connection to improved health, the biomarker serves as a clinical endpoint for evaluating clinical benefit. In one aspect, a target analyte is a biomarker.

As used in this disclosure, "intraocular fluid" refers to fluid originating within an eye, for instance aqueous or vitreous humor, liquids present in the main body of the area of the eye between the eye lens and iris and the eye lens and retina, respectively.

In one embodiment, target analyte may be selected from a protein, a protein fragment, a peptide, a polypeptide, a polypeptide fragment, an antibody, an antibody fragment, an antibody binding domain, an antigen, an antigen fragment, an antigenic determinant, an epitope, a hapten, an immunogen, an immunogen fragment, or any combination of any two or more thereof. As used in this disclosure, "target analyte" is any substance that will elicit an immune response. In particular, target analyte may relate to a peptide or protein that reacts specifically with antibodies. According some embodiments, target analyte may include a protein which has at least one epitope.

Target recognition elements specific for a target analyte may be used to detect presence or absence of the target analyte in a sample. A wide range of complementary binding or coupling partners may be used. In some cases, choice of target recognition element may be determined by target analyte to be detected, requirement for adapter molecules, and/or level of specificity required for assay. In various aspects, target recognition elements may be specific for binding or detecting proteins prevalent in intraocular fluid, such as (a) cystallins; (b) binding proteins for retinal or retinal, enzymes involved in the biosynthesis of retinal or retinal, modification, derivatization, or degradation products of retinal or retinal, for example, Retinal-binding Protein 3; and (c) other proteins such as alpha-enolase (which is a tau crystallin), Dickkopf-related protein 3, transthyretin (TTR), Prostaglandin-H2 D-isomerase, osteopontin, rhodopsin, amyloid-like proteins, and fructose bisphosphate aldolase isoform C (a.k.a. ALDOC, ALDC). In one aspect, target recognition element may be specific for α-crystallin A, CRYAA, or CRYA1.

In this disclosure, "target recognition element" refers to a substance that binds to a target analyte in a sample. Target recognition element may include an upstream assay antibody. In one aspect, target recognition element may be an antibody conjugated to a signal producing molecule. Signal-producing molecule may include a gold nanoparticle, platinum nanoparticle, carbon, colored latex, colored polystyrene bead, or magnetic bead. In one aspect, the signal-producing molecule is a fluorescent tag, an electrically-conducting tag, a functionalized electrode or field-effect transistor, or a chemical reaction producing a colorimetric, fluorescent, or electrochemical signal. In one aspect, the target recognition element is complementary to a control element.

In this disclosure, "signal producing molecule" refers to a substance that generates a detectable signal. For instance, signal producing molecule may include components such as antibody-adaptor conjugates, as described throughout this disclosure, which are designed to generate a detectable signal, thereby indicating the presence or interaction of target analyte.

As used in this disclosure, "control element" refers to a substance that is used to provide information on functioning of an assay. In some embodiments, control element may provide information on binding specificity, level of non-specific background binding, degree of binding cross-reactivity, and/or performance of assay reagents and detection system. Control element may include at least one positive control to monitor assay performance.

In one aspect, control element may include one binding partner of a complementary binding pair, wherein the other binding partner is an assay reagent. Control element may be an antibody or an antibody fragment. Control element may be complementary to a portion of target recognition element.

In another aspect, complementary binding pairs may include antibody-antigen interactions or antibody-ligand interactions.

As used in this disclosure, "test element" refers to a substance that is used to provide information on a sample tested by an assay. In some embodiments, test element may provide information including whether a sample contains proteins found at relatively high abundance in intraocular fluid compared to other fluids or interferents which are likely to be present in the sample and whose presence in the sample would not by themselves affirm that an open-globe injury has occurred. In one aspect, test element may include one binding partner of a complementary binding pair, wherein one binding partner of the complementary binding pair is a target recognition element and the other binding partner is a test element. Target recognition element may bind to a target analyte, and test element may bind to the target analyte in a different location. A complementary region of test element may be complementary to a portion of target analyte that is distinct from a portion of the target analyte that is complementary to target recognition element. In one aspect, test element may be an antibody or antibody fragment. In one aspect, the test element may be an aptamer, including a non-antibody protein with binding affinity to target analyte. In one aspect, test element may be a nucleic acid sequence or complementary nucleotide sequences. In one aspect, test element may be any molecule that is shown to bind specifically to target analyte.

As used in this disclosure "substrate" is any surface that supports an assay. Substrate may be a solid substrate or a porous substrate, for example.

In certain aspects, substrate may be a solid substrate. Examples of solid substrates include, but are not limited to, a membrane, a nitrocellulose membrane, a microtiter plate, glass, microbeads, nanoparticles, microparticles and magnetic beads. In various aspects, solid substrate may include glass beads, nanoparticles, microparticles, gold nanoparticles, magnetic beads, or paramagnetic beads.

In some embodiments, assay elements (including target recognition elements, control elements, and test elements) may be placed on substrate surface, with or without an adapter molecule between the substrate and the assay element. In some cases, assay elements may bind to substrate by covalent or non-covalent interaction. Methods of placing assay elements on substrate may include printing, spotting, or any other method. In this disclosure, "printing" can be used to include any of the methods for placing the assay elements on a membrane.

"sample" and "specimen," as used in this disclosure, are used in their broadest sense to include any composition that is obtained and/or derived from biological or environmental source, as well as sampling devices (e.g., swabs) which are brought into contact with biological or environmental samples. "Biological samples" may include body fluids such as blood, plasma, tears, or eye fluid. In one embodiment, biological sample may be fluid obtained from an injured eye, including blood and extraocular and intraocular fluid.

In various aspects, sample may be eye fluid, blood, or a tissue or fluid sample from an eye wound.

Treating may be used in this disclosure, for instance, in reference to methods of treating an eye injury or a systemic condition. Treating may include reversing, reducing, or arresting the symptoms, clinical signs, and underlying pathology of a condition in a manner to improve or stabilize a subject's condition. Treatment may include therapeutic treatment, as well as prophylactic or suppressive measures, for example for the treatment of an open-globe injury. Treatment may include protecting an eye from further external contact, administering antibiotics, and/or immediate referral to an ophthalmologist. Treatment may include a complete slit lamp eye exam, a Snellen eye chart exam, or a computed tomography scan of the face and jaws. Further, treatment may include surgically reinserting eye tissue, removing eye tissue, returning the eye to the correct intraocular pressure, and other interventions.

Figure 5:
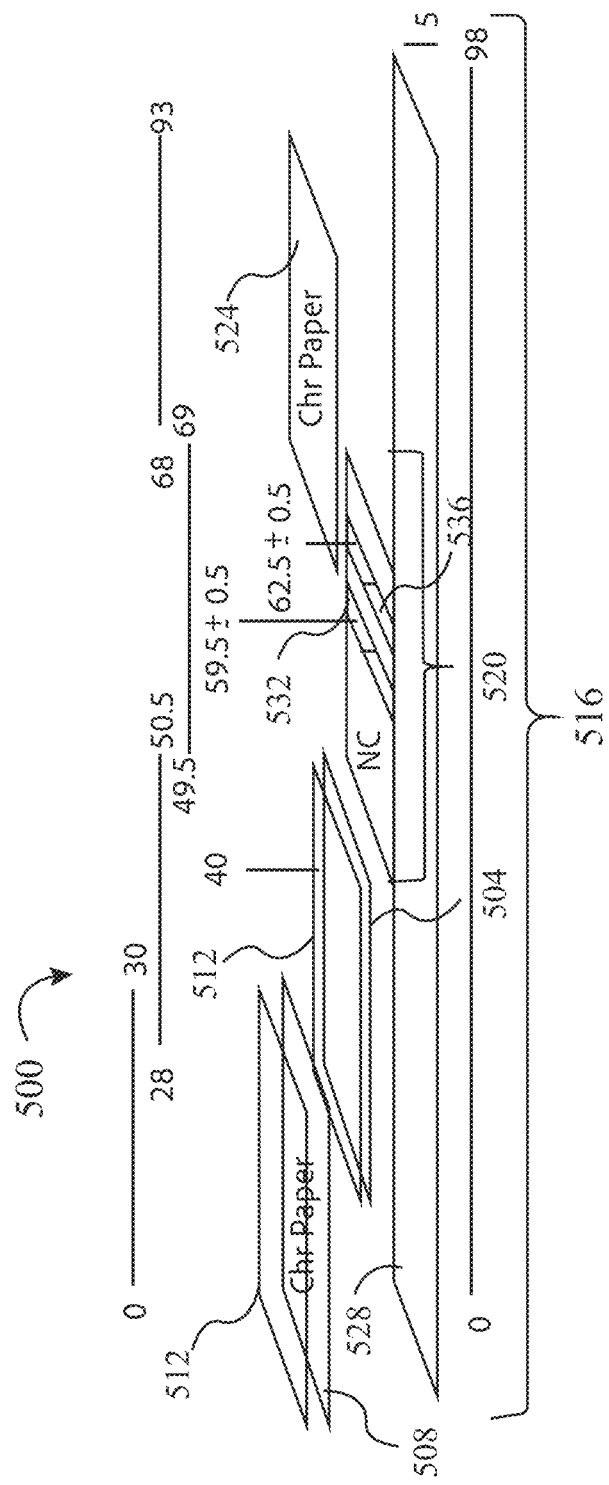
FIG. 5 illustrates a representative schematic diagram of an assay strip that shows placement coordinates of the beginning and ending of each segment of the lateral flow assay.

Referring now to FIG. 1, an exemplary embodiment of substrate 100 is schematically shown. Substrate 100 may include a sample receiver 104, a target recognition element 108, and a signal producing molecule 110, as defined above. In some embodiments, sample receiver 104 may be upstream of a conjugate pad; the conjugate pad may be upstream of a test pad; the test pad may be upstream of a wicking pad. substrate 100 may include a target recognition element 108 specific for intraocular fluid. Target recognition element 108 may contact substrate 100. Target recognition element 108 may correspond to and be able to bind to a target analyte. Substrate 100 may include a control element 120. In some cases, control element 120 may include at least one positive control to monitor assay performance. Substrate 100 may include a blood filter 112. Blood filter 112 may contact sample receiver 104 or conjugate pad. As used in this disclosure, "test pad," is an area of substrate designed to generate and/or communicate a detectable signal indicating target analyte's presence. In some cases, test pad may be part of a lateral flow assay as shown in FIG. 5 below. A "wicking pad," as used herein, is an area of substrate in an assay system that drives flow. In some cases, wicking pad may drive continuous flow of sample through assay and help facilitate proper interaction between the sample and other components, such as, for example, conjugate pad and test pad, as shown in FIG. 5 below. Substrate 100 may include a flow path 106 from sample receiver 104. Flow path may be configured to flow fluid sample and one or both of target recognition element 108 and signal producing molecule 110. In some cases, one or both of target recognition element 108 and signal producing molecule 110 are downstream of sample receiver 104 on flow path 106. A "flow path," as used in this disclosure, refers to designated route along which matter moves. For example, a sample may travel along a flow path after being received by a sample receiver. Flow path may allow fluid sample to interact with assay elements embedded within or upon substrate 100. Once fluid sample enters substrate 100 through sample receiver 104, it may follow flow path 106 towards target recognition element 108. As described above, target recognition element 108 may be specifically configured to bind with a target analyte found in intraocular fluid. In some cases, target recognition element 108's location downstream of sample receiver 104 may ensure that sample will contact it under controlled flow conditions, facilitating effective binding. In some cases, signal producing molecule 110 may be located with target recognition element 108, for instance conjugated with the target recognition element. As described above, signal producing molecule may be responsible for producing a detectable signal upon target recognition element 108's interaction with target analyte. In some cases, flow path 106 in substrate 100 may facilitate laminar flow, a condition where a fluid moves in smooth, parallel layers without turbulence. In some cases, substrate 100 and/or flow path 106 may include a microfluidic device. In some embodiments, laminar flow may help to maintain a steady, orderly progression of fluid, allowing for efficient and specific binding of target analyte with target recognition element 108. In some cases, design of flow path 106 may include selecting its dimensions and surface properties to reduce any disturbances that might disrupt this flow, thereby enhancing the accuracy and reliability of the target analyte detection.

Still referring to FIG. 1, substrate 100 may include a test element 116, as defined above, downstream from target recognition element 108 on flow path 106. Test element may be configured to bind, directly or indirectly, to target analyte. In some embodiments, a blood filter 112, as described above, may be upstream of test element 116 on flow path 106. Blood filter 112 may be configured to filter red blood cells from fluid. Substrate 100 may also include a control element 120, as defined above. Control element 120 may be located downstream from target recognition element 108 on flow path 106. Control element 120 may be configured to bind to target recognition element 108. In one aspect, substrate 100 may be a solid or porous substrate. In one aspect, substrate 100 may be a nitrocellulose membrane. Signal producing molecule 110 may include gold nanoparticles, which produce a red, pink, or purple color by surface plasmon resonance (SPR) when present in high enough concentrations within a specific surface area or volume.

In some embodiments, signal producing molecule 110 may include gold nanoparticles. Gold nanoparticles may be conjugated to target recognition element 108, which binds to target analyte (biomarker) in sample. Nanoparticle-antibody-analyte complex may flow down a nitrocellulose membrane (flow path 106 of substrate 100) until it reaches test element 116. Test element may include an antibody, which is immobilized and can simultaneously bind to target analyte at a location on its structure different from where target recognition element binds, thus immobilizing and concentrating gold nanoparticles at test element 116 (e.g., test line). In the absence of target analyte, nanoparticle-upstream antibody complex may not be immobilized at test element 116 and may flow farther down substrate 100 until it reaches control element 120. In some cases, control element 120 includes an immobilized antibody, which binds directly to target recognition element 108, concentrating gold nanoparticles on the control element (e.g., control line). In some cases, a significant fraction of antibody molecules do not manage to bind to target analyte even when present, so control line may be expected to have gold nanoparticle coloration regardless of whether the sample was positive for target analyte or not. Alternative types of molecules (e.g., fluorescent dyes, nanoparticles made of other materials) can achieve signal generation when localized in a defined location using similar or alternative mechanisms (e.g., other optical methods such as fluoresce or chromogenic chemical reactions, electrical conductivity across the membrane, or the like).

Still referring to FIG. 1, in one aspect, target recognition element 108 binds a target analyte, wherein the target analyte may be indicative of an open-globe eye wound. In an additional aspect, blood filter 112 may be in sample receiver 104 or conjugate pad. In one aspect, target analyte may be selected from a protein, a protein fragment, a peptide, a polypeptide, a polypeptide fragment, or any combination thereof. In a further aspect, target analyte may be present at a high concentration in intraocular fluids. In one aspect, a high concentration of target analyte may include concentration values greater than 5-10 ng/mL. In one aspect, a high concentration of target analyte may include concentration values less than 5 ng/ml. In one aspect, the target analyte may be present at a concentration of 0.5 to 10 ng/mL. In another aspect, the target analyte may be present at a concentration of about 2 to 5 ng/ml, about 0.5 to 2 ng/ml, about 0.05 to 0.5 ng/ml, about 0.5 to 1 ng/mL, about 1 to 2 ng/mL, about 1 to 3 ng/mL, about 1 to 4 ng/mL, or about 1 to 5 ng/mL. In a further aspect, the target analyte may be present at a concentration of about 5-10 ng/mL, about 6-10 ng/ml, about 7 to 10 ng/ml, about 8 to 10 ng/mL, about 9 to 10 ng/mL, about 5 to 6 ng/mL, about 5 to 7 ng/ml, about 6 to 7 ng/ml, about 6 to 8 ng/ml, about 6 to 9 ng/mL, or about 7 to 10 ng/mL.

Still referring to FIG. 1, in one aspect, the concentration of target analyte may be at least 2 times, at least 100 times, at least 1,000 times, at least 10,000 times, at least 100,000 times, or at least 1,000,000 times higher in intraocular fluid than in both blood and tear fluid. In one aspect, the concentration of the target analyte may be about 10 times, about 20 times, about 30 times, about 40 times, about 50 times, about 60 times, about 70 times, about 80 times, about 90 times, about 100 times, about 110 times, about 120 times, about 130 times, about 140 times, about 150 times, about 160 times, about 170 times, about 180 times, about 190 times, about 200 times, about 250 times, about 300 times, about 350 times, about 400 times, about 450 times, about 500 times, about 550 times, about 600 times, about 650 times, about 700 times, about 750 times, about 800, about 850 times, about 900 times, about 950 times, about 1,000 times, about 2,000 times, about 3,000 times, about 4,000 times, about 5,000 times, about 6,000 times, about 7,000 times, about 8,000 times, about 9,000 times, about 10,000 times, about 20,000 times, about 30,000 times, about 40,000 times, 50,000 times, about 60,000 times, about 70,000 times, about 80,000 times, about 90,000 times, about 100,000 times, about 200,000 times, about 300,000 times, about 400,000 times, about 500,000 times, about 600,000 times, about 800,000 times, about 900,000 times, or about 1,000,000 times higher in intraocular fluid than in blood and tear fluid.

Still referring to FIG. 1, in one aspect, a ratio of intraocular concentration of target analyte to blood and tear fluid concentration of the target analyte may be about 1:2, 1:10, 1:20, 1:30, 1:40, 1:50, 1:60, 1:70, 1:80, 1:90, 1:100, 1:200, 1:300, 1:400, 1:500, 1:600, 1:700, 1:800, 1:900, 1:1,000, 1:2,000, 1:3,000, 1:4,000, 1:5,000, 1:6,000, 1:7,000, 1:8,000, 1:9,000, 1:10,000, 1:50,000, 1:100,000, 1:200,000, 1:300,000, 1:400,000, 1:500,000, 1:600,000, 1:700,000, 1:800,000, 1:900,000, or 1:1,000,000 times higher, or over 1:1,000,000 times higher in the intraocular fluid than in blood and tear fluid. In one aspect, the ratio of the intraocular concentration of the target analyte to the blood and tear fluid concentration of the target analyte may be between about 1:2 to 1:100, between about 1:100 to 1:1,000, between about 1:1,000 to 1:10,000, between about 1:10,000 to 1:100,000, or between about 1:100,000 to 1:1,000,000, between about 1:2 to 1:50, 1:50 to 1:100, 1:100 to 1:200, 1:200 to 1:300, 1:300 to 1:400, 1:400 to 1:500, 1:500 to 1:600, 1:600 to 1:700, 1:700 to 1:800, 1:800 to 1:900, 1:900 to 1:1,000, 1:1,000 to 1:1500, 1:1,500 to 1:2,000, 1:2,000 to 1:2,500, 1:2,500 to 1:3,000, 1:3,000 to 1:3500, 1:3,500 to 1:4,000, 1:4,000 to 1:4,500, 1:4,500 to 1:5,000, 1:5,000 to 1:5,500, 1:5,500 to 1:6,000, 1:6,000 to 1:6,500, 1:6,500 to 1:7,000, 1:7,000 to 1:7,500, 1:7,500 to 1:8,000, 1:8,000 to 1:8,500, 1:8,500 to 1:9,000, 1:9,000 to 1:9,500, 1:9,500 to 1:10,000, 1:10,000 to 1:50,000, 1:50,000 to 1:100,000, 1:100,000 to 1:200,000, 1:200,000 to 1:300,000, 1:300,000 to 1:400,000, 1:400,000 to 1:500,000, 1:500,000 to 1:600,000, 1:600,000 to 1:700,000, 1:700,000 to 1:800,000, 1:800,000 to 1:900,000, or 1:900,000 to 1:1,000,000.

Still referring to FIG. 1, in another aspect, target analyte may be present at a low concentration in extraocular fluids. In one aspect, target analyte may be α-crystallin A (CRYAA) protein. In an additional aspect, target analyte may be at least 90% identical to SEQ ID NO:1. In a further aspect, the target analyte includes at least six consecutive amino acids of SEQ ID NO:1. In another aspect, the target analyte may be SEQ ID NO:1. In one aspect, the techniques described herein relate to substrate 100, wherein target recognition element 108 may be selected from a protein, a protein fragment, a binding protein (BP), a binding protein fragment, or any combination thereof. In an additional aspect, the target analyte may be at least 90% identical to SEQ ID NO:2. In a further aspect, the target analyte includes at least six consecutive amino acids of SEQ ID NO:2. In another aspect, the target analyte may be SEQ ID NO:2. In an additional aspect, target recognition element 108 may be selected from an antibody, an antibody fragment, or any combination thereof. In a further aspect, the antibody fragment may be an antibody heavy chain, an antibody light chain, a single chain antibody, a single-domain antibody, a Fab antibody fragment, an Fc antibody fragment, an Fv antibody fragment, a F(ab') 2 antibody fragment, a Fab' antibody fragment, a single-chain Fv (scFv) antibody fragment, an antibody binding domain, or any combination thereof. In another aspect, target recognition element 108 may be selected from an antigen, an antigenic determinant, an epitope, a hapten, an immunogen, an immunogen fragment, or any combination thereof.

The term "identical" as used herein is the extent of sequence homology, which may be determined using any computer program and associated parameters known in the art, such as BLAST 2.2.2 or PASTA version 3.0t78, for instance with the default parameters. Protein and/or nucleic acid sequence identities (homologies) may be evaluated using any of the variety of sequence comparison algorithms and programs known in the art. The term "essentially identical" or "substantially identical" refers to a sequence that has at least 85% sequence identity with the sequence referred to. For example, the sequence of a nucleic acid molecule is substantially identical to a given nucleic acid sequence if it has 90% or more sequence identity with the same. As a further example, the sequence of a peptide or protein is substantially identical to a given amino acid sequence if it has 90% or more sequence identity with the same. A sequence essentially identical or substantially identical with another sequence may also be a sequence that has at least 91%, 92%, 93%, 94%, 95%, 96%, 97%, 98%, 99% or 100% sequence identity to the sequence referred to.

Still referring to FIG. 1, assay techniques used in conjunction with substrates and/or lateral flow assay (LFA) devices include any of a number of colorimetric enzyme-linked assays. In one aspect, assay techniques may be based upon formation of a complex between a complementary binding pair, followed by detection with a colorimetric detection system comprising an enzyme-conjugate label and a colorimetric substrate 100 or LFA device. In another aspect, assay techniques may be based upon formation of a complex between a complementary binding pair, followed by detection with a fluorescent detection system. In a further aspect, assay techniques may be based upon formation of a complex between a complementary binding pair, followed by detection with a surface plasmon resonance system. Detection system may include enzyme-linked immunosorbent assays (ELISA), though a skilled person would appreciate that such techniques are not restricted to the use of antibodies but are equally applicable to any colorimetric, fluorescent, or surface plasmon resonance assay. In one aspect, a surface plasmon resonance assay may include a colorimetric assay.

Still referring to FIG. 1, in one embodiment, ELISA may include a sandwich assay format. In this format, target analyte to be measured may be bound between two antibodies-a capture antibody (e.g., target recognition element) and a detection antibody (e.g., test element). In another embodiment, ELISA may include a non-competitive assay, in which a primary antibody may bind to a capture antigen and an amount of bound antibody is determined by a secondary detection antibody. In one aspect, an upstream assay reagent and test-line/test element antibodies may be primary antibodies, while the control-line/control element antibody may be a secondary antibody. Either monoclonal or polyclonal antibodies may be used as capture and/or detection antibodies in sandwich ELISA systems. Monoclonal antibodies have a mono specificity toward a single epitope that allows fine detection and quantitation of small differences in antigen. A polyclonal antibody can also be used as the capture antibody to bind as much of the antigen as possible, followed by the use of a monoclonal antibody as the detecting antibody in the sandwich assay to provide improved specificity. A monoclonal antibody can also be used as the capture antibody to provide specific analyte capture, followed by the use of a polyclonal antibody as the detection antibody in the sandwich assay. Additionally, both capture and/or detection antibodies could be monoclonal.

Still referring to FIG. 1, as used in this disclosure, "antibody" refers to immunoglobulin molecules and immunologically active portions of immunoglobulin molecules, i.e., molecules that contain an antigen binding site that immunospecifically binds an antigen. In some cases, native antibodies and intact immunoglobulins, or the like, may be heterotetrameric glycoproteins of about 150,000 daltons, composed of two identical light (L) chains and two identical heavy (H) chains. Light chains from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively.

Experimentally, antibodies can be cleaved with proteolytic enzyme papain, which causes heavy chains to break, producing three separate antibody fragments. Two units that consist of a light chain and a fragment of heavy chain approximately equal in mass to light chain are called Fab fragments (i.e., the "antigen binding" fragments). A third unit, consisting of two equal segments of heavy chain, is called Fc fragment. Fc fragment may be uninvolved in antigen-antibody binding. Fc fragment may be important in later processes involved in ridding one's body of an antigen. As used in this disclosure, "Fv" is a minimum antibody fragment that contains a complete antigen-recognition and -binding site. In some cases, Fv may consist of a dimer of one heavy- and one light-chain variable domain in tight, non-covalent association. In this configuration, three complementarity-determining regions (CDRs) of each variable domain may interact to define an antigen-binding site on a surface of VH-VL dimer. Collectively, the six CDRs may confer antigen-binding specificity to the antibody. However, even a single variable domain (or half of an Fv comprising only three CDRs specific for an antigen) may have an ability to recognize and bind to an antigen, although typically at a lower affinity than an entire binding site. "Single-chain Fv" or "scFv" antibody fragments may include VH and VL domains of antibody, wherein these domains are present in a single polypeptide chain. In some cases, the Fv polypeptide further includes a polypeptide linker between the VH and VL domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

Still referring to FIG. 1, antibodies may include naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., Science 246:1275-1281, 1989, which is incorporated herein by reference). These and other methods of making, for example, chimeric, humanized, CDR-grafted, single chain, and bifunctional antibodies are well known (Winter and Harris, Immunol. Today 14:243-246, 1993; Ward et al., Nature 341:544-546, 1989; Harlow and Lane, Antibodies: A laboratory manual (Cold Spring Harbor Laboratory Press, 1999); Hilyard et al., Protein Engineering: A practical approach (IRL Press 1992); Borrabeck, Antibody Engineering, 2d ed. (Oxford University Press 1995); each of which is incorporated herein by reference). In addition, modified or derivatized antibodies, or antigen binding fragments of antibodies, such as pegylated (polyethylene glycol modified) antibodies, can be useful for the present methods. As such, antibodies may include Fab, F(ab')2, Fd and Fv fragments of an antibody that retain specific binding activity.

Still referring to FIG. 1, as used in this disclosure "secondary antibody" refers to an antibody that will bind a target analyte and that is conjugated with either a signal producing molecule 110, also referred to as an adaptor molecule herein, such as biotin, or an enzyme label such as horseradish peroxidase (HRP). Antibody-adaptor conjugates may be processed to give a detectable result by contacting the antibody-adaptor conjugate with an adaptor-enzyme conjugate and then the enzyme substrate 100; for example, antibody-biotin conjugates bind streptavidin-HRP conjugates. Antibody-enzyme label conjugates may include antibody-HRP conjugates. Use of secondary antibodies is discussed and exemplified below. When HRP is used, secondary antibody with enzyme may be specific for upstream assay antibody (e.g., target recognition element) and not for test line antibody (e.g., test element); the test line and upstream assay antibodies may have significantly different binding sites for secondary antibodies.

Still referring to FIG. 1, as used in this disclosure the term "binds specifically" or "specific binding activity" or the like, means that two molecules form a complex that is relatively stable under physiologic conditions. In some cases, the term is also applicable where, an antigen-binding domain is specific for a particular epitope, which is carried by a number of antigens, in which case the antibody carrying the antigen-binding domain are able to bind to the various antigens carrying the epitope. Specific binding may be characterized by a high affinity of antibody to antigen. In some cases, affinity constant measures binding specificity of antigen to antibody and is usually measured by the equilibrium dissociation constant between the antibody and its antigen (Ko). In some cases, binding may be considered specific when affinity constant is about $1 \times 10^{-6}$ M, generally at least about $1 \times 10^{-7}$ M, usually at least about $1 \times 10^{-8}$ M, and particularly at least about $1 \times 10^{-9}$ M or less. Specific binding may also be characterized by antibody or antigen-binding domain not binding strongly to anything that is not a target. An antibody that binds specifically to an antigen may have low levels of off-target molecules.

Still referring to FIG. 1, in some cases, capture and detection antibodies of each binding pair recognizes two non-overlapping epitopes so that when an antigen binds to a capture antibody, the epitope recognized by a test element 116 is not obscured or altered. In one aspect, an enzyme-conjugate label includes an enzyme selected from a list including horseradish peroxidase, alkaline phosphatase, β-D-galactosidase or glucose oxidase. In an additional aspect, enzyme label may be conjugated directly to a primary antibody or introduced through a secondary antibody that recognizes primary antibody. It may also be conjugated to a protein such as streptavidin if the primary antibody is biotin labelled. In one aspect, a secondary antibody conjugated to an enzyme is specific for the upstream target recognition antibody and not for the test line antibody. In one aspect, assay detection system may include a detection substrate selected from the list including gold, silver, and aluminum. In one aspect, the detection substrate may include a gold nanoparticle (AuNP) conjugated to an antibody (Ab-AuNP).

Still referring to FIG. 1, assay device for detection of open-globe injuries could also be used for development of novel and emerging IA formats, which are based on advances in complementary technologies. Some examples of such prospective IA formats are wash-free IA based on FRET (fluorescence resonance energy transfer) or CRET (chemiluminescence resonance energy transfer); signal-enhanced IA based on the use of nanoparticle-based signal detection step or the use of micro- and submicro-beads for binding capture antibodies/antigens; rapid multiplex IAs based on Lab-in-a-tube technology, and vertical microfluidics, including fluorescent gold nanorod technology.

Still referring to FIG. 1, substrate 100 may be particularly amenable to use in kits for detection of target analytes. Such kits may comprise substrates together with instructions and any assay consumables required. Different kits are envisaged for different target analytes and types of array. In one embodiment, methods for detecting an analyte in a sample comprising providing substrate 100 may include adding at least one sample to substrate 100 and processing substrate 100 such that a detectable result is provided. In one aspect, a detectable result includes two or more of at least one positive control. In one aspect, a test area result or signal output resembles that of positive control if target analyte is present in sample.

FIGS. 2A-2C illustrates use of one embodiment of an assay device 200 in the field. Assay device 200 may include substrate 100 and additional components listed below. To test an eye, swab 204 may contact eye for a certain amount of time. Swab 204 may then be removed and placed in a readout case 228. In some cases, a certain amount of time may refer to a period sufficient for sample collection and safe for patient comfort. For example, swab may collect sample for 3-5 seconds; this brief duration may ensure that the swab absorbs enough intraocular fluid to be useful for testing, without causing discomfort or injury to the eye. In another example, swab may collect sample for $10^{-15}$ seconds; this slightly longer duration might be necessary for swabs that are less absorbent or when a larger sample volume is needed. Amount of time swab is used to collect sample may allow for thorough contact with fluid without extending so long as to cause excessive discomfort or reflex tearing, which might dilute the sample. Swab 204 may include absorbent material attached to the end of a stick or similar handle, used for collecting and delivering a fluid sample, specifically intraocular fluid, into the substrate for analysis. Swab 204 may include embodiments and material similar to sample receiver 104 as described above.

Still referring to FIGS. 2A-2C, for use in low-light situations, in some embodiments, a light button 212 may illuminate a display window 224 with display lights 220. Light button 212 may include a user-activated control, typically positioned for easy access, that when pressed, activates the lighting mechanism. Button may feature a tactile design for easy identification by touch in dark environments and could be equipped with a momentary switch that illuminates display only while pressed, conserving battery life. Display window 224 may refer to an area of device where information is shown to user. This may be a screen or a panel integrated into device, for example made from a transparent or translucent material that allows light from the display lights to illuminate the information presented. Display lights 220 may include lights used to illuminate display window 224. They may be light emitting diodes (LEDs) due to their efficiency, longevity, and capability to provide clear, bright light without significant power consumption. Positioning of these lights may be around a perimeter of display window or behind it to ensure even distribution of light across the entire display area.

Still referring to FIGS. 2A-2C a rubberized grip 216 may also be included. In some cases, after substrate 200 is placed in readout case 228, sample is processed, and control and test results appear in display window 224, with either test or control results shown in reading zone 208. Reading zone 208 may be a transparent window that allows assay results to be viewed when the assay device 200 is placed into readout case 228. Reading zone 208 may include a non-digital embodiment, a transparent window through which physical assay results can be directly observed. This window part may be made from a clear, durable material such as glass or high-grade plastic that ensures unobstructed visibility. Users manually place the substrate into a readout case, aligning it such that the reading zone overlays the area where test results are displayed. Results might appear as color changes, lines, or other visual markers that indicate the presence or concentration of a target analyte. This method relies on visual inspection without any electronic components, requiring adequate lighting and sometimes magnification tools to accurately interpret the results. In another embodiment, reading zone 208 may include a digital environment enhanced with electronic components that digitize the process of reading and interpreting assay results. Upon inserting the substrate into the readout case, embedded sensors or cameras within the case capture images of the assay results displayed through the transparent window. This digital capture may be then processed by onboard computing systems, which use image processing algorithms to analyze the results. The data is quantified, and the outcome is displayed on a digital screen integrated into the readout case or transmitted to an external device such as a computer or smartphone. This digital approach allows for more precise and automated result analysis, reducing human error and providing capabilities for storing, sharing, and further analyzing results electronically. This system can also include connectivity features, enabling real-time data syncing with healthcare databases or remote consultation with specialists. Embodiment 200 may also include a computing system that enables it to effectively manage critical functionalities like light control, power management, and displaying test results of the assay. This system may be powered by a microcontroller or microprocessor. For light control, the system may adjust the intensity and duration of the display lights based on ambient light conditions or user settings, enhancing visibility while conserving power. Regarding power management, the computing system may include algorithms designed to optimize battery usage, such as by dimming lights or shutting down inactive components, thereby extending the device's operational life. When it comes to displaying test results, the system may process data collected from the assay, interpret it based on preloaded diagnostic criteria, and then clearly display these results on the device's screen for easy reading by health professionals. This setup not only ensures accuracy and efficiency in testing but also enhances the usability and functionality of the device in clinical settings.

Figure 3:
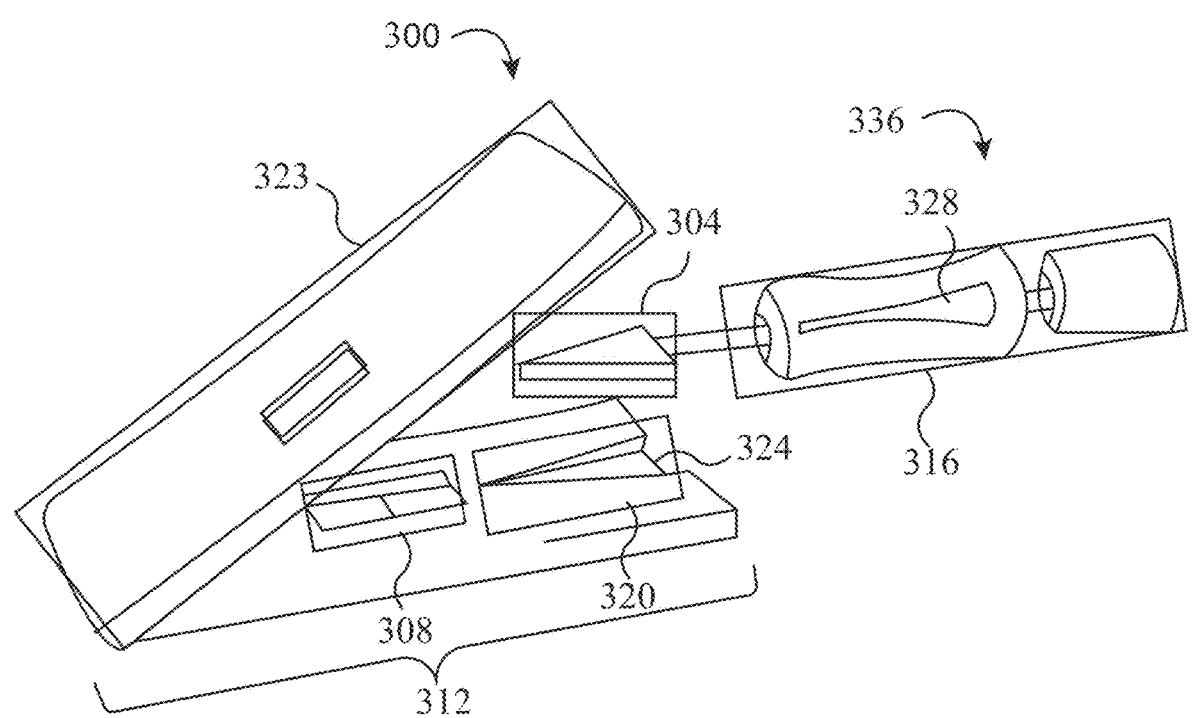
FIG. 3 illustrates an embodiment of an assay device.

Referring now to FIG. 3 an embodiment of an assay device 300 is illustrated. Assay device 300 may include embodiments and material as described above. Assay device 300 may include a sampler tool 336 with a soft, pointed, highly absorbent pad or swab 304 attached to the sampler tool 336, wherein the swab 304 contacts the eye and collects a sample from the patient. Sampler tool 336 may include a plurality of components attached together working in union to extract a sample of a patient to be placed into an assay, substrate, and the like. Sampler tool 336 may broadly cover embodiments including syringes, running buffers, integrated or non-integrated swabs, and the like as described throughout this disclosure. Sampler tool 336 May refer to an apparatus with a connection between all the selected elements. Swab 304 may be attached to a handling element 316 containing a running buffer solution 328. A "running buffer solution," as used herein, is a formulated liquid that maintains a controlled environment around the biological sample during an assay. Its primary function is to ensure the proper pH, ionic strength, and stability of the environment so that the biochemical reactions can occur under optimal conditions. The buffer may also contain additional components like detergents to prevent nonspecific binding, preservatives to extend shelf life, and agents to enhance the visibility of the assay results. For example, a running buffer may include Sodium chloride, potassium chloride, disodium hydrogen phosphate, Tris-Buffered Saline (TBS), sodium borate, Tris base, acetic acid, and EDTA (EthylenediaminetetraAcetic acid), and the like. Swab 304 may be placed in the sample input area 320, which houses the conjugate pad 324. In one aspect, conjugate pad 324 is made of fiberglass. Swab 304 may be held in close contact with conjugate pad 324 with an optional hinged cover 332 that closes onto the hard plastic casing 312. Running buffer solution 328 may be then pushed through the handling element 316 onto conjugate pad 324. Results of the test are read in the display window 308.

Figure 2:
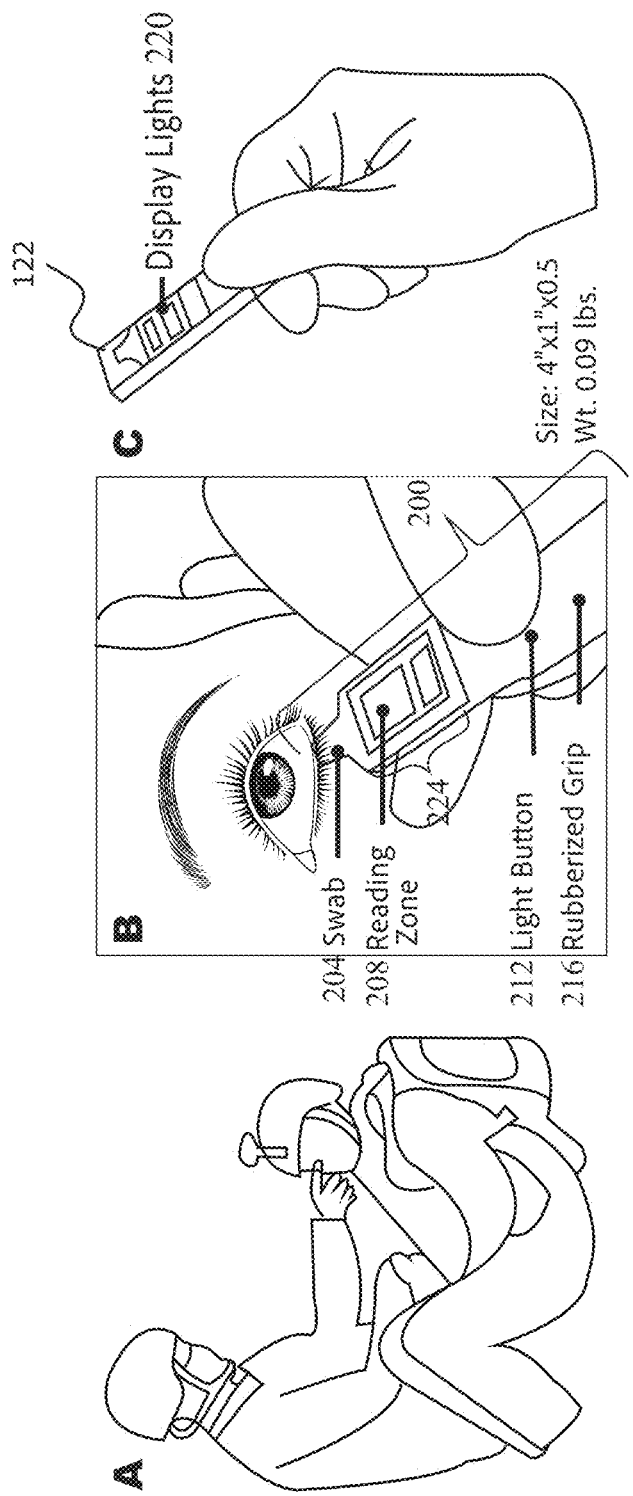
FIG. 2 illustrates use of one embodiment of an assay device in the field.
Figure 4:
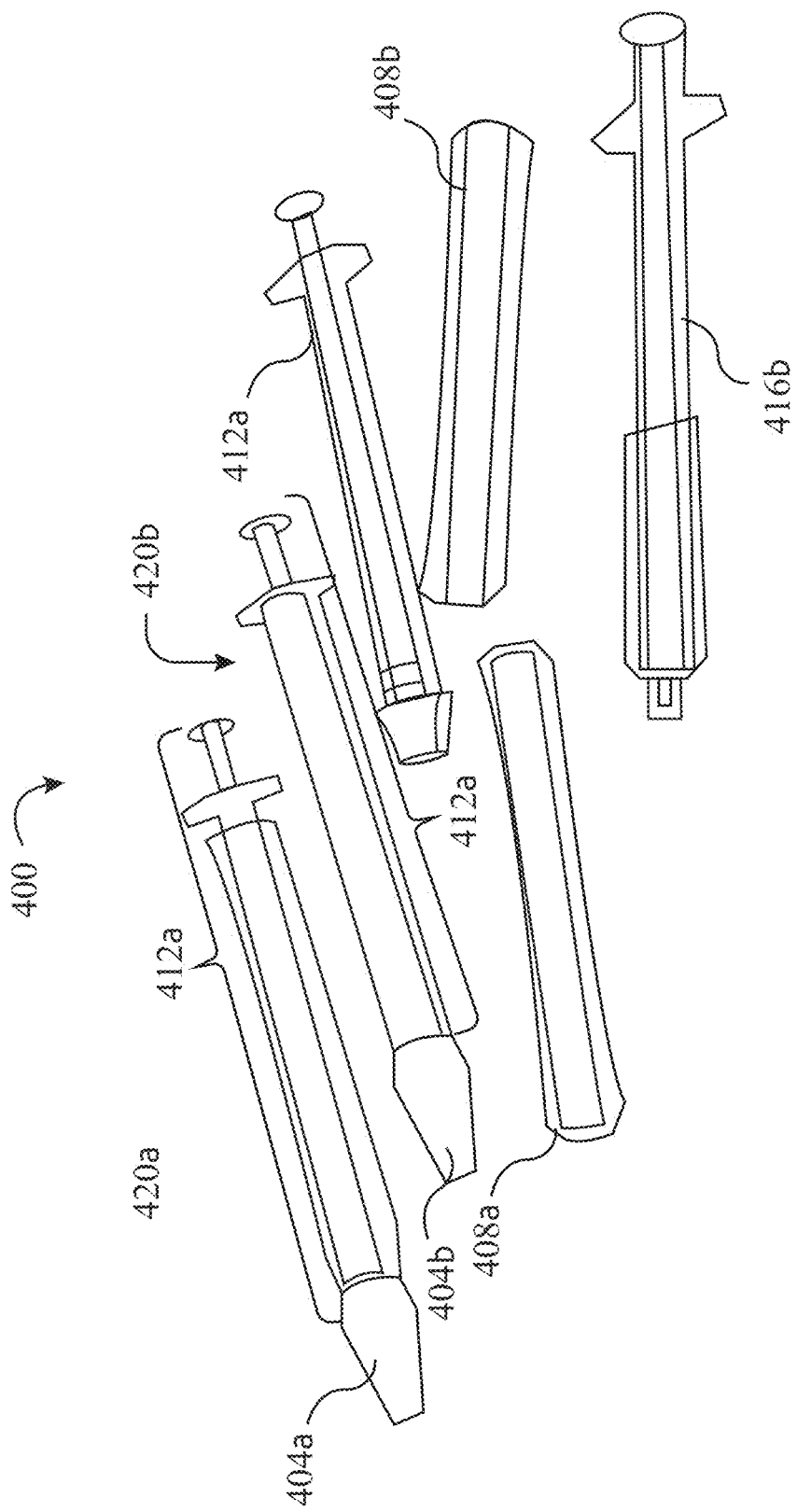
FIG. 4 illustrates sampler tool embodiments.

Referring to FIG. 4, sampler tool embodiments 400 are illustrated. Sampler tool embodiments 400 may include material and embodiments as described above. This device is meant to sample an injured eye; eyes with full-thickness, open-globe injuries may no longer have firm eye walls and therefore could be susceptible to further deformation, injury, and intraocular content extrusion if the sampling device places significant pressure on the ocular surface. This device therefore includes a specialized sampler tool that can be used to collect fluid from the eye surface while minimizing contact pressure. One embodiment of a sampler tool 420*a* includes a swab 404*a* attached to a handling element 412*a* filled with a running buffer. Another embodiment of a sampler tool 420*b* includes a swab 404*b* attached to a handling element 412*b* filled with running buffer 328. Handling elements 412*a* and 412*b* may include a syringe 416*a* or 416*b* and may also include a pinch grip 408*a* or 408*b*. The sampler tool 420 may include a roughly pencil-shaped cylinder with an ergonomic pinch grip 408 and a pointed tip swab 404 made of a highly absorbent material: one type of absorbent material may include a rayon blend (e.g., "ShamWow" shammy cloth). In one aspect, the absorbent material may include one or more of synthetic polymer foam, cotton, rayon, or bamboo. Once swab 404 has absorbed the sample, swab 404 is pressed onto the conjugate pad 324; an optional hinged cover 332 for the hard plastic casing 312 of the device is shown in one embodiment of the device, which closes onto the hard plastic casing to press the tip onto conjugate pad 324 to promote fluid transfer, as shown in FIG. 2. In one embodiment, the swab 204, 304, or 404 is pressed onto the sample input area 320. In one embodiment of sampler tool 420, sampler tool 420 is a pencil-shaped cylinder and includes syringe 416 filled with running buffer, pinch grip 408, and swab 404. The syringe filled with this buffer solution serves dual purposes. Firstly, it allows for the precise application of the fluid sample onto the assay strip. This can be critical for tests where the volume and placement of the sample influence the accuracy and reliability of the results. Secondly, the syringe dispenses the running buffer across the assay strip. Once the sample is applied, the buffer solution flows through the strip, carrying the sample along the test's pathway. This movement facilitates the interaction between the sample and any specific reagents or indicators placed on the strip. As the sample migrates, it encounters different zones that may indicate the presence or absence of certain analytes through a change in color or another detectable signal. This method of using a syringe to apply both the sample and the running buffer simplifies the testing process, reduces the number of steps required, and helps to standardize the volume and flow rate, thereby enhancing the consistency and reliability of the test results. It is particularly useful in point-of-care settings where quick, reliable results are necessary, and technical resources may be limited.

Still referring to FIG. 4, after swab 404 has contacted the sample and the sample has been absorbed into swab 404, swab 404 is pressed onto conjugate pad 324. The running buffer is applied onto conjugate pad 324 with the syringe after the sample has begun to interact with antibody-AuNP conjugates. In some aspects, the running buffer is applied to conjugate pad 324. Applying the sample directly to conjugate pad 324 may increase the sensitivity of the assay for cases of very small open-globe wounds.

Referring now to FIG. 5, a representative schematic diagram 500 of an assay strip that shows placement coordinates of the beginning and ending of each segment of the lateral flow assay is illustrated. Coordinate units are in millimeters. The means by which a target analyte in the sample is recognized and used to produce a detectable signal is via a sandwich immunoassay. Enzyme-linked immunosorbent assays (ELISAs) are one example of a sandwich immunoassay used in this invention. Sandwich Immunoassays used for the current invention include monoclonal-polyclonal sandwich Immunoassays, antigen-down immunoassays, competitive inhibition immunoassays, and rapid Immunoassays. Sandwich immunoassays detect target analytes through conjugation to target recognition elements in the device. The target recognition elements may include antibodies, some of which are conjugated to signal-producing molecules such as gold nanoparticles (AuNPs), gold nanorods, carbon, colored latex, fluorescent tags, electrically conductive tags, electrically conductive nanoparticles, colored polystyrene beads, or magnetic beads. In some embodiments, secondary antibodies are conjugated with an adaptor molecule such as biotin, and also bind the target analyte. Signal-producing molecules that are AuNPs produce a red signal when concentrated on a surface, via surface plasmon resonance.

Still referring to FIG. 5, the first, or upstream, target recognition element may be attached to a signal-producing molecule. The upstream target recognition element conjugated to a signal-producing molecule may be the first element to contact the sample, and flows with the sample while attaching to target analytes in the sample at a first location on the target analyte. The second, downstream, target recognition elements are also referred to as target recognition elements. The target recognition elements are immobilized in the capture and readout area of the device. At least two kinds of target recognition elements are used: a test element and a control element. Each target recognition element may be deposited and immobilized in a different line in the capture area. As the sample containing the upstream target recognition element flows past the test element, the test element binds to the target analyte at a second location on the target analyte. The test element only produces a signal if the target analyte may be present in the sample, as the target analyte serves as a bridge connecting the upstream target recognition element and the test element. As the sample containing the upstream target recognition element flows past the control element, the control element binds directly to the upstream recognition element. The signal producing molecule, conjugated to the upstream recognition element, produces a signal on the control line when the upstream recognition element binds to the control element. The assay strip 516 may include overlapping strips of paper and paper-like materials that carry a sample-containing fluid from a sample receiver 508 to a wicking pad 524 via capillary action. The overlapping strips may include: a sample receiver 508 made of chromatography paper, a conjugate pad 504; a test pad 520 made of nitrocellulose, with test line antibodies 532 and control line antibodies 536 immobilized on the test pad 520; and a wicking pad 524. In some embodiments, a blood filter 512 may be present on top of the conjugate pad 504. In some embodiments, a blood filter 512 may be present on top of the sample receiver 508. In additional embodiments, the conjugate pad 504 has the upstream target recognition element deposited on a first surface of the conjugate pad. In some embodiments, the conjugate pad may be made of fiberglass, and the upstream target recognition element may be an antibody-AuNP conjugate. In one aspect, the blood filter 512 may be composed of fiberglass with a first porosity, and the conjugate pad 504 may be composed of fiberglass with a second porosity.

In one embodiment, the sample may be applied to the sample receiver 508, then a running buffer may be added to the sample receiver 508 to propel the sample farther down the strip. A blood filter 512 made of fiberglass may be present on top of the conjugate pad 504, between the conjugate pad 504 and the sample receiver 508. In another embodiment, there may be no blood filter 512, and the sample may be applied directly to the conjugate pad 504, which may be made of fiberglass. After the sample may be applied to the conjugate pad 504, running buffer may be applied to the sample receiver 508. In some aspects, the running buffer may be applied to the conjugate pad 504. In some aspects, the running buffer may be applied to the blood filter 512 above the conjugate pad 504. Applying the sample directly to the blood filter 512 above the conjugate pad 324, or directly to the conjugate pad 504, may increase the sensitivity of the assay for cases of very small open-globe wounds. The segments of the assay strip 516 overlap each other according to FIG. 4, and are adhered to a water-repellent backing material 528. One example of a suitable water-repellent backing material 528 may be parafilm. In one aspect, that water-repellent backing material may be one or more of parafilm, laminated paper or cardboard.

Figure 6:
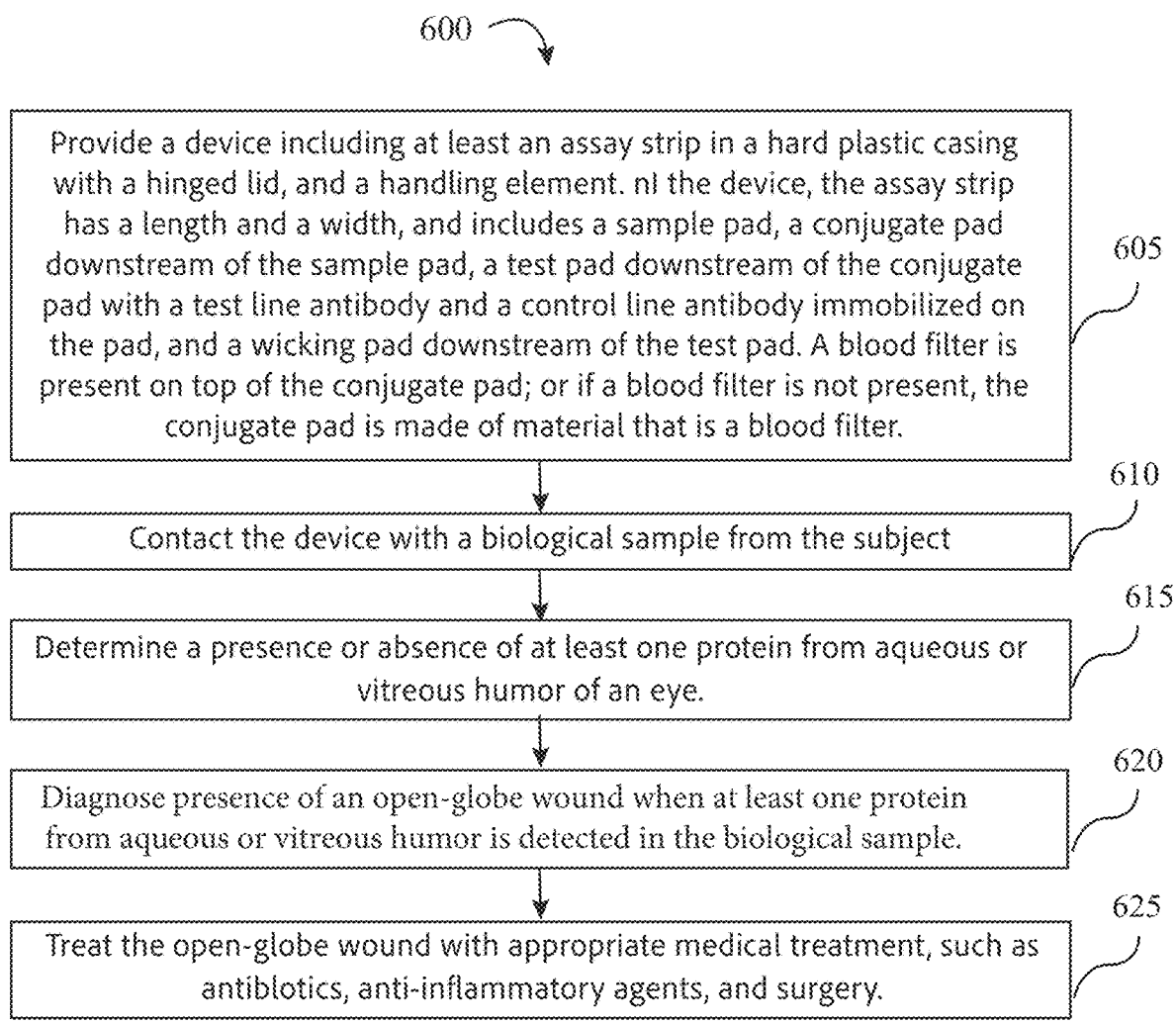
FIG. 6 illustrates a method of treating an open-globe wound.

Referring now to FIG. 6, a method 600 of treating an open-globe wound is illustrated. Method 600 may implement devices and methods as described herein and with reference to FIGS. 1-5. At step 605, method 600 includes providing a device including at least an assay strip in a hard plastic casing with a hinged lid, and a handling element. In the device, the assay strip has a length and a width, and includes a sample receiver, a conjugate pad downstream of the sample receiver, a test pad downstream of the conjugate pad with a test line antibody and a control line antibody immobilized on the pad, and a wicking pad downstream of the test pad. A blood filter may be present on top of the conjugate pad; or if a blood filter may be not present, the conjugate pad may be made of material that may be a blood filter. At step 610, method 600 includes contacting the device with a biological sample from the subject. At step 615, method 600 includes determining a presence or absence of at least one protein from aqueous or vitreous humor of an eye. At step 620, method 600 includes diagnosing a presence of an open-globe wound when at least one protein from aqueous or vitreous humor may be detected in the biological sample. At step 625, method 600 includes treating the open-globe wound with appropriate medical treatment, such as antibiotics, anti-inflammatory agents, and surgery. The method and assay described are one example of a method and device for detecting and treating an open-globe eye wound.

Referring now to FIG. 7, a method 700 of use for a substrate is illustrated. Method 600 may implement devices and methods as described herein and with reference to FIGS. 1-6. At step 705, method 700 includes receiving, using a sample receiver, a fluid sample. At step 710, method 700 includes binding, using a target recognition element specific to intraocular fluid in fluidic communication with the sample receiver, to a target analyte. At step 715, method 700 includes signaling, using a signal producing molecule, the binding of the target recognition element specific to intraocular fluid with the target analyte.

Figure 8:
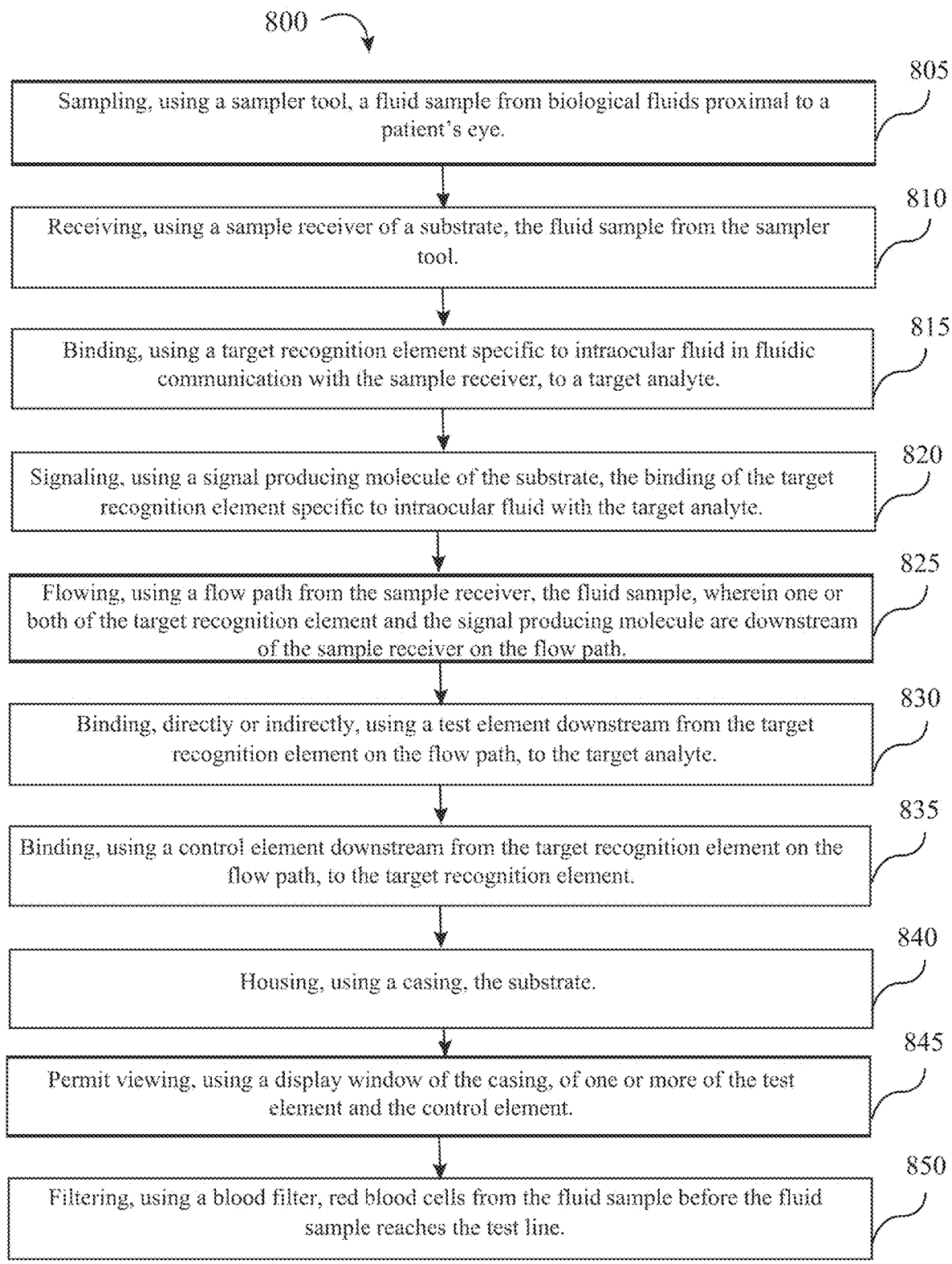
FIG. 8 illustrates a method of using a fieldable open-globe eye detection system.

Referring now to FIG. 8, a method 800 of using a fieldable open-globe eye detection system is illustrated. Method 600 may implement devices and methods as described herein and with reference to FIGS. 1-7. sampling, using a sampler tool, a fluid sample from biological fluids proximal to a patient's eye. At step 805, method 800 includes receiving, using a sample receiver of a substrate, the fluid sample from the sampler tool. At step 810, method 800 binding, using a target recognition element specific to intraocular fluid in fluidic communication with the sample receiver, to a target analyte. At step 815, method 800 signaling, using a signal producing molecule of the substrate, the binding of the target recognition element specific to intraocular fluid with the target analyte. At step 820, method 800 flowing, using a flow path from the sample receiver, the fluid sample, wherein one or both of the target recognition element and the signal producing molecule are downstream of the sample receiver on the flow path. At step 825, method 800 binding, directly or indirectly, using a test element downstream from the target recognition element on the flow path, to the target analyte. At step 830, method 800 binding, using a control element downstream from the target recognition element on the flow path, to the target recognition element. At step 835, method 800 housing, using a casing, the substrate. At step 840, method 800 permit viewing, using a display window of the casing, of one or more of the test element and the control element. At step 845, method 800 filtering, using a blood filter, red blood cells from the fluid sample before the fluid sample reaches the test line.

With reference to FIGS. 1-8, the preferred target analyte that this device is enabled to detect is α-Crystallin A (a.k.a. Crystallin-αA, αA-Crystallin, CRYAA, CRYA1); a synonymous name for this protein is Heat Shock Protein Beta-4 (HSPB4). This target is chosen because of its high concentrations in intraocular fluids (aqueous humor and vitreous humor) and relatively low concentrations in extraocular fluids that would be likely to be present on the eye surface in the event of an eye injury (e.g., blood and tear fluid); therefore, CRYAA is present in significant amounts on the eye surface to be sampled if that eye is injured in a manner that resulted in an open-globe. Various aspects of this disclosure include detecting this protein in -a Lateral Flow Assay device (LFA), using an LFA to diagnose open-globe injuries, as well as the specific CRYAA-binding antibody reagents. These antibodies were generated using a synthetic immunogen sequence that was designed to enable the resulting antibodies to bind to both human and rabbit homologs of CRYAA protein (to allow for their use in both pre-clinical animal trials and clinical trials in humans), while being unlikely to bind to the human HSPB6 protein, which is the most similar human protein to CRYAA/HSPB4 that was not found to be intra-ocular specific based on protein levels in various bodily fluids. As the largest differences between human and rabbit CRYAA and human HSPB6 appear at the C-terminal ends of the proteins, this region of the CRYAA protein was used as the basis for the immunogen sequence. The immunogen protein sequence used was as follows (read from N-terminal residue to C-terminal residue): SADGMLTFSGPKIQTGLDATHAERAIPVSREEKPT-SAPS (SEQ ID NO:2)

To create an immune response, this immunogen was conjugated to both BSA (Bovine Serum Albumin) and KLH (Keyhole Limpet Hemocyanin) in two separate reactions via a cysteine residue added synthetically to the N-terminus of the immunogen and then added either individually or together in the same animal multiple times. The immunogen was also designed to approximate the most abundant configuration of post-translational modifications that would be present over a typical human lifespan that did not include major instances of eye-affecting illness or injury; this included a truncation of the C-terminal serine residue (the C-terminus of the target analyte ends in PTSAPS §. (SEQ ID NO:3), with the last 'S' truncated in most young adults and older) and a mutation of a cysteine residue in the protein sequence MLTFCGPKIQ (SEQ ID NO: 4) to a serine residue in the immunogen MLTF §.GPKIQ (SEQ ID NO:5) to prevent the synthetic immunogen from forming dimers linked at the cysteine residues, as these dimers make up a minority of the CRYAA proteins in most humans. No other single post-translational modifications (serine phosphorylation, asparagine/glutamine deamidation, GlcNAcylation, etc.) were noted to be present in the majority of CRYAA proteins, and so these were not included in the immunogen sequence. In some aspects, the immunogen sequence has an added cysteine residue on the N-terminal end to allow for conjugation with KLH, BSA, or a combination thereof, to promote an immune response. Sequences described herein are set forth in Table 1.

The present invention is designed to diagnose open-globe injuries for warfighters in the field. Additional users include hospitals and clinics, and the device is also appropriate for inclusion in first aid kits found in homes and businesses in sectors such as research laboratories, manufacturing, construction, or other businesses that employ facilities maintenance personnel.

TABLE 1

Sequences used in designing the assay.

| Protein | Sequence |
| --- | --- |
| Human Alpha-Crystallin A (SEQ ID NO:1) | MDVTIQHPWF KRTLGPFYPS RLFDQFFGEG LFEYDLLPFL SSTISPYYRQ SLFRTVLDSG ISEVRSDRDK FVIFLDVKHF SPEDLTVKVQ DDFVEIHGKH NERQDDHGYI SREFHRRYR LPSNVDQSAL SCSLSADGML TFCGPKIQTG LDATHAERAI PVSREEKPTS APSS |

TABLE 1-continued

Sequences used in designing the assay.

| Protein | Sequence |
|---|---|
| Modified C-terminus of Human Alpha-Crystallin A (SEQ ID NO: 2) | SADGMLTFSG PKIQTGLDAT HAERAIPVSR EEKPTSAPS |
| Truncated C-terminus end of Human Alpha-Crystallin A SEQ ID NO: 3 | PTSAPSS |
| Unmodified portion of Human Alpha-Crystallin A SEQ ID NO: 4 | MLTFCGPKIQ |
| Modified portion of Human Alpha-Crystallin A SEQ ID NO:5 | MLTFSGPKIQ |

Examples

The following examples are provided to further illustrate the embodiments of the present invention but are not intended to limit the scope of the invention. While they are typical of those that might be used, other procedures, methodologies, or techniques known to those skilled in the art may alternatively be used.

Example 1: Biomarker Development

To develop appropriate biomarkers for detection using device, several criteria may be used. Overall, biomarkers allow for distinguishing between ocular surfaces with open-globe injuries and ocular surfaces without open-globe injuries. Criteria for biomarker evaluation may include: (1) consistent concentrations in relevant bodily fluids across individuals; (2) high ratio of concentration between intraocular fluids and extraocular fluids; high enough concentration in intraocular fluids to surpass sample limits of detection from swabs of ocular surfaces with full-thickness defects; and, (3) low enough concentration in extraocular fluids to not display a positive when device strip is saturated with these fluids.

Ex vivo samples of relevant fluids and eye tissues from rabbits and humans are obtained for evaluation of the assay. Intraocular fluids sampled include aqueous humor and vitreous humor; extraocular fluids include whole blood and tear fluid. These fluids are available from humans, and fluids applicable to the present invention, except tear fluid, are available from rabbits. Targeted proteomic analyses using liquid chromatography/mass spectrometry (LC-MS) with multiple reaction monitoring are used to quantify specific proteins within each sample; these specific proteins were identified from literature and database reviews as being likely to meet the aforementioned biomarker evaluation criteria.

Correlations between potential marker concentrations in human and rabbit fluids ensure that animal model experiments for device validation (see Example 6) reflect medically relevant situations. If the validation studies from later Examples (see Examples 4 and 6) show an inability of the device to consistently and specifically identify the marker and distinguish between eyes with open-globe injuries and eyes with intact surfaces, then proteomics analysis of each ex vivo sample is performed to identify additional peaks that meet the biomarker criteria.

Example 2: Reagent Development

After determining the biomarker(s) associated with ocular leakage discovered in Example 1, novel antibodies are developed for diagnostic device for each marker to be detected. Commercially available antibodies were not used for the prototype. These antibodies were discovered and custom made using the methods described above combined with typical antibody discovery and development workflows performed with mice.

Multiple markers are developed to reduce false positive or false negative readouts during device testing. The antibody development phase has several steps which involve feasibility assessment and assay design, antibody conjugation labeling and pairwise antibody selection for sandwich ELISA, and development and optimization.

Synthesis of gold nanoparticle (AuNP)-antibody conjugates entails continuously synthesizing and optimizing the conjugation formulations that are deposited onto the assay strip of the devices. Assay and device performance feedback generated during subsequent examples is used to achieve optimal AuNP-antibody formulations and optimal conditions for immobilization and storage in the devices. Several parameters are evaluated to achieve optimal assay results, including AuNP diameter, AuNP concentration, pH of the conjugation reaction with the antibody, and antibody concentrations.

Commercially available antibodies may theoretically be used for both AuNP-antibody conjugates and for the target recognition antibodies. When a commercial antibody is not available for a desired biomarker, additional antibodies are developed for identified biomarkers. Specific antigens are produced using techniques such as recombinant synthesis, followed by development of novel monoclonal antibodies by commercial vendors. The resulting novel antibodies are then integrated into the reagents for the LFA devices.

The AuNPs are commercially sourced. Prior to the functionalization of the AuNPs with different antibodies, AuNPs are derivatized with thiolated-polyethylene glycol (PEG). The efficiency of the coupling protocol is assessed using commercially available fast colorimetric protein determination kits, and the colloidal stability of the constructs is assessed by dynamic light scattering (DLS). Upstream antibodies were not linked to gold nanoparticles using thiol chemistry in the prototype; instead, gold nanoparticles functionalized with carboxyl groups were conjugated to amines on the antibodies via EDC/sNHS chemistry (EDC: 1-Ethyl-3-(3-(dimethylamino) propyl) carbodiimide; sNHS: N-hydroxysulfosuccinimide).

The first iteration of reagent formulation includes pass/fail criteria such as color change during antigen binding that is clearly observed. If the color change during antigen binding is not clearly observed, an alternative synthesis protocol is applied.

Example 3: Optimize LFA device

Multiple devices are readily produced to enable highly parallel experiments to be performed, allowing the evaluation of multiple device configurations and reagent formulations to be tested in a highly efficient and simultaneous manner. Optimization of design parameters includes optimizing concentration of immobilized antibodies, optimization of the pH and ionic strength of immobilized buffers, and optimization of sample volume used for the assay. Several devices are fabricated in an identical manner, each with a different AuNP-antibody conjugate concentration immobilized on the reagent storage zone. These devices are treated with an identical sample (e.g., a specific volume, antigen concentration, etc.), and the resulting capture layer is imaged and the results are correlated with the initial AuNP-antibody concentration to determine the optimal concentration range.

The first objective is 1) to determine the reagent conditions and device configurations/operation conditions to detect one biomarker in a sample of defined concentration within approximately 5 min. These conditions are used as the baseline conditions for subsequent development and optimization of the second objective, 2) demonstration that the LFA device can successfully detect the biomarkers of interest at clinically relevant concentrations.

Example 4: In Vitro Verification and Protocol Development

Using the devices produced in Example 3, the optimized prototypes studies are verified with samples prepared with the selected biomarkers, e.g., PBS and other fluids representative of the aqueous or vitreous humor. These samples are formulated with known concentrations of the biomarkers. Aqueous and vitreous humor is tested as pre-extracted samples or as removed from excised eyes; rabbit and human fluids are also used for this example. These samples are used to determine baseline performance of the LFA device.

Additional features such as the amount of sample fluid and the proper handling technique are determined. The in vitro studies are used to guide the surgical team performing the in vivo device validation studies to develop a protocol for device packaging. The in vitro study is used as preliminary pre-clinical data. Analytical performance is verified with these data to demonstrate that the assay detects the biomarkers at physiologically relevant concentrations.

The LFA devices are tested in the presence of interferents, such as blood. There are many interfering compounds within blood, including endogenous antibodies that demonstrate cross-reactivity to either the biomarker, or to the capture antibodies of the device. Hemolysis of the red blood cells also results in release of hemoglobin which is an interferent. Any observed interfering effects from blood and investigate the specific components involved are evaluated. Other compounds such as drugs, aspirin or lidocaine, may also induce interference with immunoassays. The effect of each interferent is studied as a function of their concentration. The results of these experiments are used to refine the reagent formulation in Example 6. The assay demonstrates acceptable performance for biomarker detection in the presence of at least 2 potential interferents. For this experiment, 25 α-CRYAA antibodies from our custom antibody discovery vendor were received. Best pair using rabbit intraocular fluid samples were determined to be MAB1601 Conjugate and MAB1301 T-line. This pair was used in animal model studies. Sensitivity may be further increased by higher Conjugate loading or T-line concentration. Sequencing Results for Complementarity Determining Regions of MAB1301 (Test Line Ab) and MAB1601 (Conjugate Ab) are illustrated in FIG. 9. Light Chain CDRs were the same in both; heavy chains show large differences.

Example 5: Prototype Shelf-Life Testing, Sterilization, and Packaging

LFA devices are assembled, and reagents added as determined in the previous examples. These samples are exposed to an 'Accelerated' Storage test, which entails incubation in a precision-controlled environmental chamber, e.g., at 40° C. ±2° C. and relative humidity (RH) of 5%. Other temperature ranges from −30 to 50° C. are also studied. Multiple groups of samples are prepared and incubated together, so that one group can be removed and tested at different time points, (e.g., 1 month, 3 months, 6 months). The assay performance is compared to similar samples prepared immediately before testing and not incubated in the chamber. Multiple concentrations of the reagents immobilized on the paper devices are also tested to evaluate the effect of concentration on any observed degradation.

Samples are incubated m the environmental chamber at the appropriate temperature/humidity for the first set of multi-month accelerated tests. The samples are then evaluated to determine resulting changes in assay performance.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Example 6: In Vitro Verification

Analgesics, pain relievers, have been noted in some literature sources to potentially inhibit the activity of antibodies. Therefore relevant concentrations of two analgesic compounds were included within the samples to determine whether the test strip results would remain robust to their presence. Aspirin was included at its typical working concentration in blood (~100 μg/mL) when added to samples. Lidocaine, which is typically applied topically as gel at 5% concentration, was prepared as a saturated solution in PBS to account for reasonable worse-case scenarios with respect to the amount absorbed by the sampler tool. In anticipation of a potential decrease in signal due to these interferents, the amount of conjugate antibody loading in these tests increased from 6 μL to 8 μL. Three different concentrations of test-line antibody loading on the nitrocellulose membrane were also tested. 10 μL of sample were added to the conjugate pads of each test before applying ~100-150 μL of running buffer. Twelve strips, each using different reagent and sample conditions, were tested. FIG. 10 illustrates reagent and sample conditions for analgesic interferent experiment.

Referring now to FIG. 10, reagent and sample conditions are defined in a matrix for twelve tests. Columns show, from left to right, test number, reagent conditions, and sample conditions. Reagent conditions include (1) Conjugate Ab loading in µL; and (2) test line Ab concentration in mg/mL. Sample conditions include (1) Sample aqueous humor volume in µL; (2) sample vitreous humor volume in in µL; (3) sample aspirin stock volume (1 mg/mL concentration) in µL; (4) sample lidocaine stock volume (saturated) in µL; (5) sample human whole blood volume in µL; (6) sample PBS volume in µL; and (7) sample total volume in µL. Negative control tests included Group A, test nos. 1-3, which were blood, and Group C, test nos. 7-9 which were blood and analgesics. Positive tests included Group B, test nos. 4-6, which included blood, aqueous humor, and vitreous humor, and Group D, test nos. 10-12, which included blood, analgesics, aqueous humor, and vitreous humor.

Figure 11:
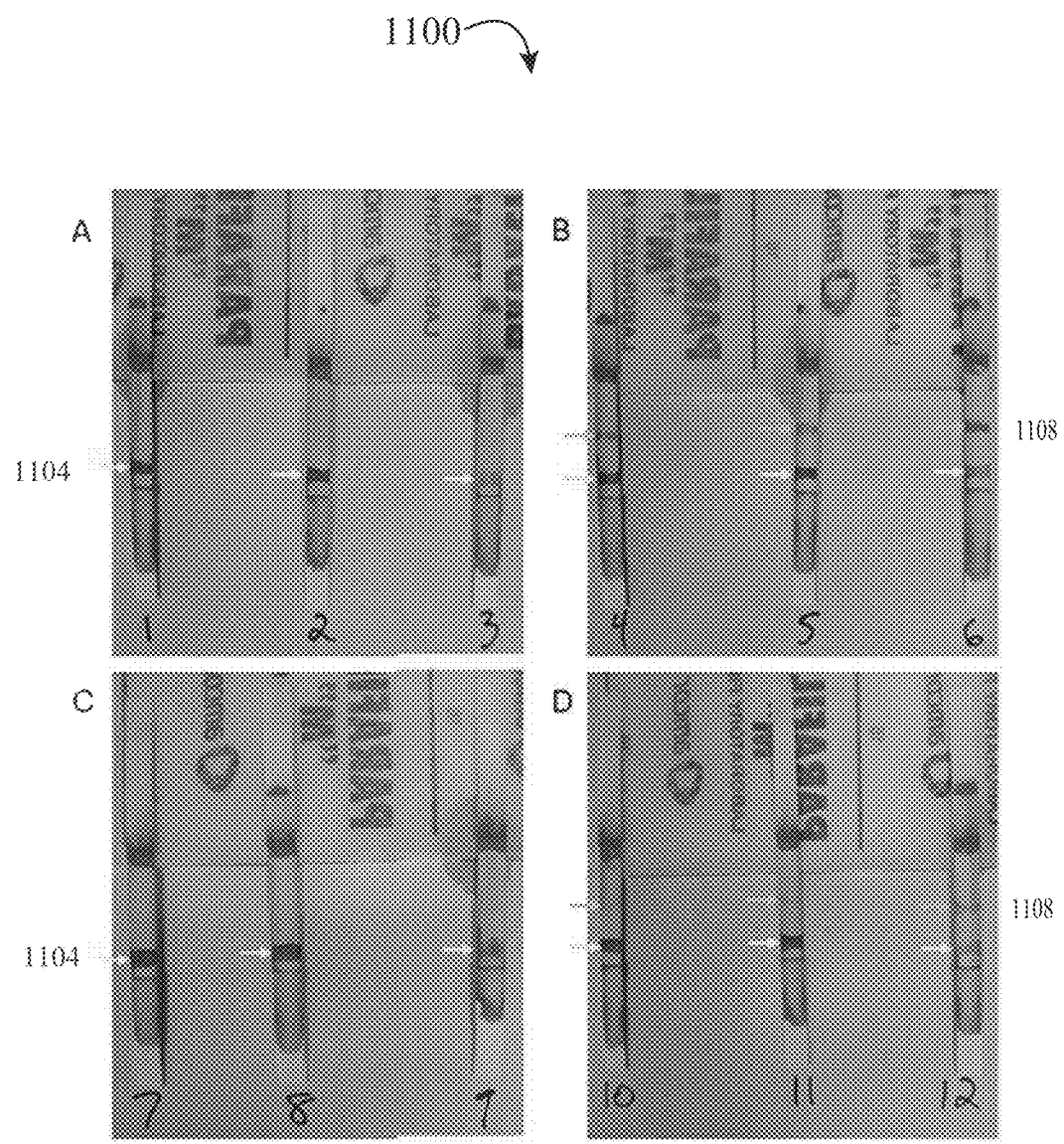
FIG. 11 illustrates test strips with different sample mixtures after ~15 minutes of run time.

Referring now to FIG. 11, results of test nos. 1-12 are shown. FIG. 11 shows test strips for: (Group A) no intraocular fluid, no analgesic; (Group B) with intraocular fluid, no analgesic; (Group C) no intraocular fluid, with analgesic; and (Group D) with intraocular fluid, with analgesic. The results showed perfect agreement between tests run with samples that contained intraocular fluids and tests with visible test-lines. The prototype is therefore robust to simultaneous blood and analgesic confounders at physiological concentrations of the target. It is noted that in the presence of analgesics seemed to significantly reduce the test line signals; fortunately, it can be demonstrated that increasing the concentration of deposited test line antibodies enhanced this signal enough to fully counteract any effects from the analgesics. Test strips with different sample mixtures after ~15 minutes of run time. Arrows 1104 point to the control lines, and arrows 1108 point to visible test lines.

Example 7: Pre-Clinical, Diagnostic In Vivo Validation Study Part 1

Test Summary:

Sample arms (3 rabbits per arm) include unwounded control eyes, surface wounds at the limbus (not full-thickness) and two different types of open-globe injuries: 3 mm lacerations and 1 mm punctures. "Arms," may refer to distinct groups or conditions within the experiment. Each arm undergoes a different treatment or intervention, allowing researchers to compare outcomes across these varied conditions. These wounds are administered in different locations on the eye, such as the anterior chamber and posterior chamber. Samples from the eyes are acquired and tested at different time points post-injury to determine the degree of wound sealing over time, and therefore, an estimate of the duration post-injury for which the device is used to detect open-globe wounds. Images of the diagnostic readout are used to confirm the success of the diagnostic device. In parallel, verification of the biomarkers' presence in the sample are measured by targeted proteomic analysis. Experimental design included: Pre-study trial to verify wounding and usage of device—2 rabbits; Day 1: Corneal Injury; Slit lamp imaging to verify injury; Day 1: Measurement with device at 15 mins, and other time point(s) 8 hrs; Day 2: Measurement with device at time point 24 hrs if necessary; and Day 2: Collect corneas for histological analysis. Summary of results from the study: Surface (closed-globe) wounds gave nearly exclusively negative results (one measurement was inconclusive); All 3 mm open-globe injuries produced positive test results at time of injury; Blood clotting or resealing in the limbus region may have caused negative results at later times; Resealing in the peripheral cornea region may have caused negative results at later times; Only a few 1 mm open-globe injuries gave positive results; Peripheral cornea (PC) wounds were more likely than limbus wounds to provide positive results.

FIG. 12 illustrates a table summarizing the pre-clinical, diagnostic in vivo validation study administration. FIG. 12 columns include (1) arm; (2) injury size; (3) injury depth; (4) injury location; (5) confounder; (6) eyes (rabbits); and (7) assay time points. FIG. 12 has a row for each arm of the study.

Test Protocol Report:

After successful demonstration of the device performance with in vitro and ex vivo samples, the effectiveness of the handheld bioassay for ocular leakage detection is verified in rabbit models of ocular wounds. Multiple New Zealand White rabbits are used for the study arms.

Species, Strain, Sex, Age, Weight, Supplier:
Species: Rabbit
Strain: New Zealand White
Sex: Female
DOB: Mar. 25, 2024
Age Range: ~12 weeks old at study initiation
Weight Range: 2.1-2.8 kg upon arrival at test facility
Supplier: Western Oregon Rabbit Company The rabbit is a species that is commonly used for non-clinical ocular toxicity studies with human drugs. The rabbit is a standard non-rodent species used in toxicology studies based upon substantial amounts of published historical data. The number of animals used in this study is considered the minimum required to achieve the objective of the study for assessment of tolerability of the test article, account for variability among animals, and assay for systemic exposure of the test article. All animals were housed in a group of 2 under standard animal care conditions with enhanced enrichment for rabbits. The rabbits were coupled according to treatment arm during the study. 12 hours light/12 hours dark, except when room lights were turned on/off during the normal cycle to accommodate study procedures. All animals had access to Certified PMI Rabbit Diet. Water was available ad libitum to each animal via an automatic watering device. No contaminants are known to be present in the water at levels that would be expected to have interfered with the results of this study. All animals arrived with an ear tattoo of a 4-digit ID number for tracking and all animal information is stored in a local MS Access database. Treatment of animals was in accordance with the study protocol and standard EyeCRO animal handling procedures which adhere to the regulations outlined in the USDA Animal Welfare Act (9 CFR Parts 1, 2 and 3) and the conditions specified in the Guide for the Care and Use of Laboratory Animals (ILAR publication, 1996, National Academy Press). The EyeCRO IACUC approved the study protocol prior to finalization to ensure compliance with acceptable standard animal welfare and humane care.

Study Design
Baseline: Pre-study trial to verify wounding and usage of device
Day 1: Corneal Injury; Slit lamp imaging to verify injury
Day 1: Measurement with device at 15 mins, and 8 hours post injury
Day 2: Measurement with device at 24 hours post injury
Day 2: Collect corneas for histological analysis Prior to wounding, the rabbits were administered an analgesic, Ketoprofen, via subcutaneous (SC) injection. A single drop of topical proparacaine was then administered as a local anesthetic. Systemic anesthesia was then performed by intraperitoneal (IP) injection of ketamine/xylazine. Additional pain management was achieved by subcutaneous (SC) injections of ketoprofen or buprenorphine at the time of wounding and at eight hours post-wounding.

Corneal injury was induced in either the limbal area or the peripheral cornea using one of three methods: (1) Surface: 3 mm lacerations were performed using a #11 scalpel to create a 3 mm wound halfway through the depth of the thickness of the sclera; (2) Full-thickness: 3 mm lacerations were performed using a #11 scalpel to induce a 3 mm fully through the sclera/cornea; and (3) 1 mm puncture wounds were performed using a 20 G needle to create a 1 mm puncture wound all the way through the sclera or cornea. A slit-lamp and camera (HαAg-Streit BM 900) were used to document the wound immediately after wounding. Images were calibrated to a standard and the size of the wound was measured/determined using Nikon NIS-Elements software (v. 5.3).

Following wounding, two samples were obtained. For the first sample, the sampler tool of the device was used to collect tears/discharge created by the wound and contralateral eyes as control. Measurements made by the device were recorded and documented at 15 minutes, 8 hours, and 24 hours post-wounding. Liquid film from the surface of the eye was collected by placing the absorbent swab as close to the wound as possible until saturated. For study arms designated with Blood Confounder, following sample collection from the eye, the absorbent swab was briefly submerged/dipped in a ~15 μL droplet of whole blood placed on a hydrophobic film surface (Parafilm). The collected fluid in the swab was applied with slight pressure into to the Blood Filter/Conjugate Pad area of the test strip, allowed to absorb into the pad, and then a running buffer was applied to the running buffer pad (on the end of the strip closer to the sample pad) to carry the sample through the test strip. Following running buffer application, at either 15 minutes, or once all red/purple coloration had passed to the readout area, whichever was last, the results were documented. The expected results were that either one, or two, distinct red lines would form on the readout area of the test strip. The bottom half of the readout area on the nitrocellulose strip was expected to always show a red line (control), while appearance of the second line confirmed a positive result. The results were documented and whole test strip was imaged after removing the top of its plastic casing. The test strips were labelled and shipped on cold packs. For the second sample, $10^{-30}$ μL (as much as possible up to 30 μL) of the remaining ocular film was drawn by pipette and deposited in a microcentrifuge tube labeled with identities corresponding to the test strips. To this liquid sample, an equal volume of RNAlater solution was added and the sample was stored at $-80°$ C. until shipment to the client on dry ice. Following sedation, rabbits were euthanized by intravenous barbiturate overdose. Euthasol® was delivered via the marginal ear vein at a concentration of 390 mg/ml, and a dose of 87 mg/kg. Following confirmation of euthanasia, whole corneas with sclera rims were collected and immediately placed in PBS. The medium was then exchanged for freshly made 4% PFA and tissue was fixed at room temperature for 23 hours. The tissue was then embedded in paraffin and shipped for further analysis. Twice daily (a.m. and p.m.), health checks were performed on rabbits for evidence of death or impending death prior to terminal sacrifice.

All study animals survived until their scheduled termination. There were no deviations to experiments for the study proper following pre-study trial testing of device use. Ocular wounding was induced as (1) 3 mm surface lacerations to the AC/limbus; (2) 3 mm full-thickness lacerations to either the AC/limbus, or the peripheral cornea; or, (3) 1 mm full-thickness punctures to either the AC/limbus, or the peripheral cornea. Each test was conducted either in the presence or absence of a blood confounder. Analysis of test strips was conducted by two separate observers to determine either a positive (test line present) or negative result (no test line present). Observer 1 conducted the test immediately upon use of the test device, whereas Observer 2 based observations off images acquired during testing. Therefore, the results obtained by Observer 1 are deemed more accurate and used to describe results.

Results

Initial Inconsistent Results in Pre-trial Experiment

In the pre-trial experiment, the two wounds to the live rabbit eyes included a 3 mm surface laceration, and a 3 mm full-thickness laceration. For the rabbit with the surface laceration, both the wounded eye and unwounded eye were sampled 15 minutes after wounding. For the rabbit with the full-thickness laceration, the wounded eye was sampled at 15 minutes, 8 hours, and 24 hours after injury; for the 24 hour time point, one test sample was taken as normal, while an additional test sample included rabbit blood that was mixed with the sample prior to pressing the sampler tool to the conjugate pad of the assay device. Representative test results for the pre-trial experiment are in FIG. 13.

Figure 13:
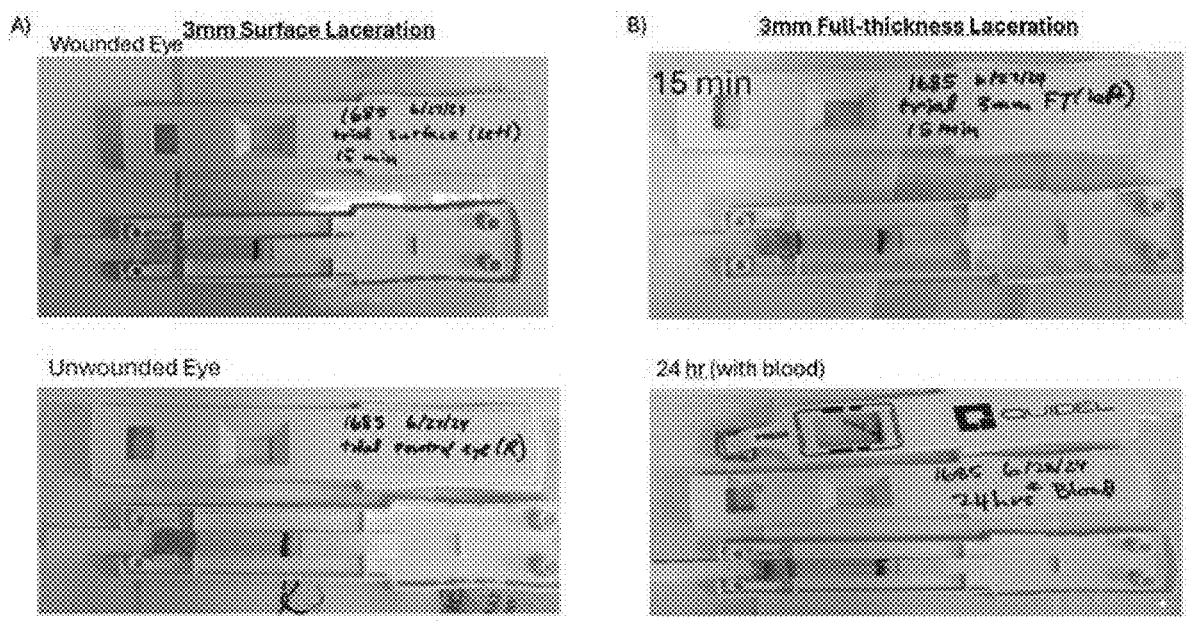
FIG. 13 illustrates LFA results from A) the rabbit receiving a surface wound and B) the rabbit receiving a full-thickness wound.

FIG. 13 illustrates LFA results from (A) the rabbit receiving a surface wound; and (B) the rabbit receiving a full-thickness wound. The results showed that, while the tests seemed to be properly run, only a single line (the control line) is seen for all four tests. A series of experiments were performed to determine why the full-thickness samples did not result in a positive test line. It was found that these initial tests behaved inconsistently, while all other tests that were made in which reagents were freshly deposited on the assay devices performed as expected.

Therefore it was determined that the problem with the tests occurred somewhere between the freezing, lyophilization, and storage processes for the tests. This most likely resulted in the aggregation of the antibody-gold nanoparticle conjugate. Because the rest of trial could not be delayed while determining the exact cause of the problem, fresh reagent stocks and an SOP were sent out for depositing them onto the strip prior to use of the device so that they can achieve consistent results.

Trial Results

The main portion of the tests used the fresh reagents and protocol sent in. FIG. 12 shows the order of the main portion of the trial. FIGS. 14-23 illustrate a table of 10 test results, from each of three different eyes at each time point. The presence of a star in the bottom left corner of a picture indicates that the user believes the test line has appeared to give a positive result of an open-globe injury. Black lines drawn on the back casing of the device indicate where the fresh test line was deposited. Slip-lamp images for each eye verifying that each wound was administered properly (not shown).

Figure 14:
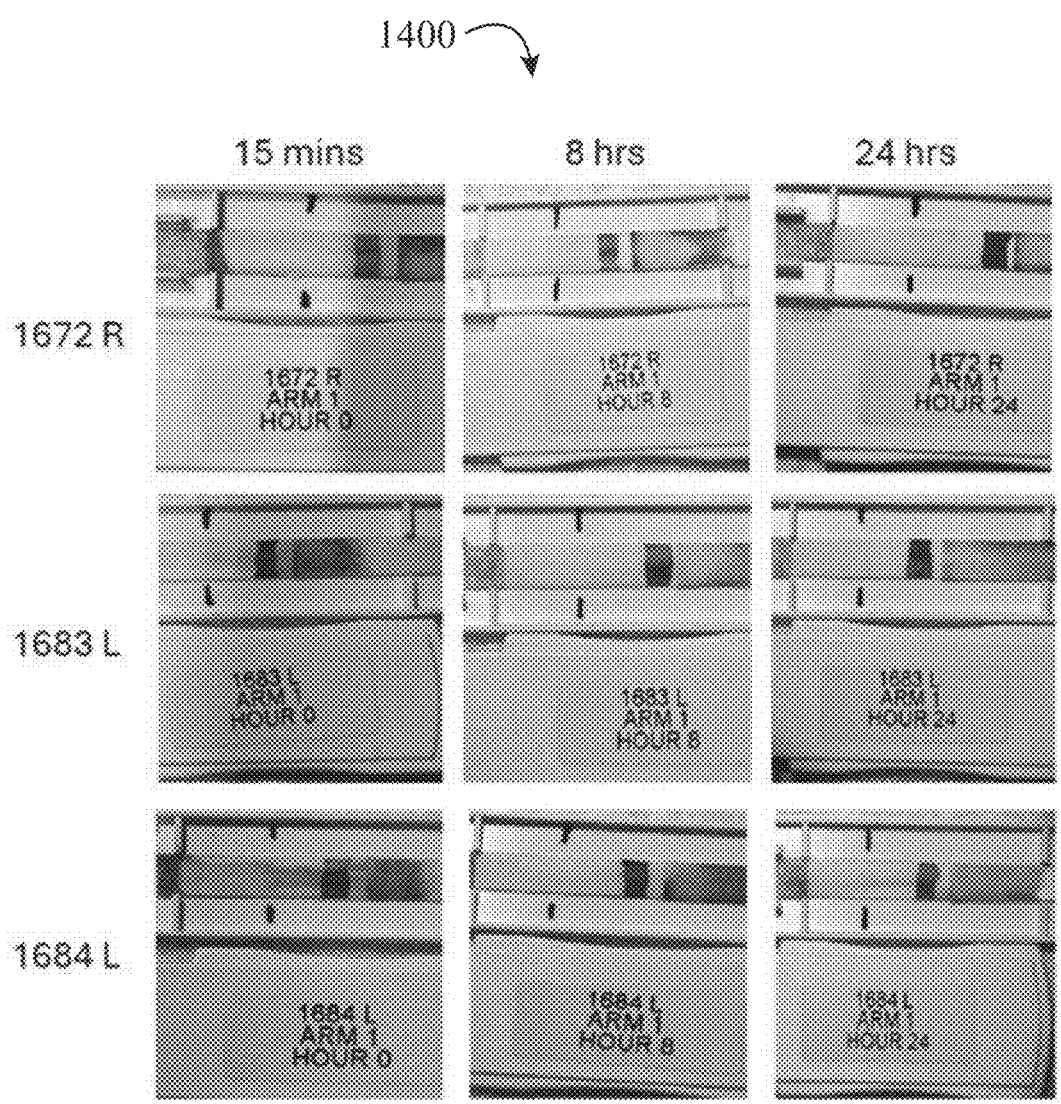
FIG. 14 illustrates results from Arm 1 wounded eyes.
Figure 15:
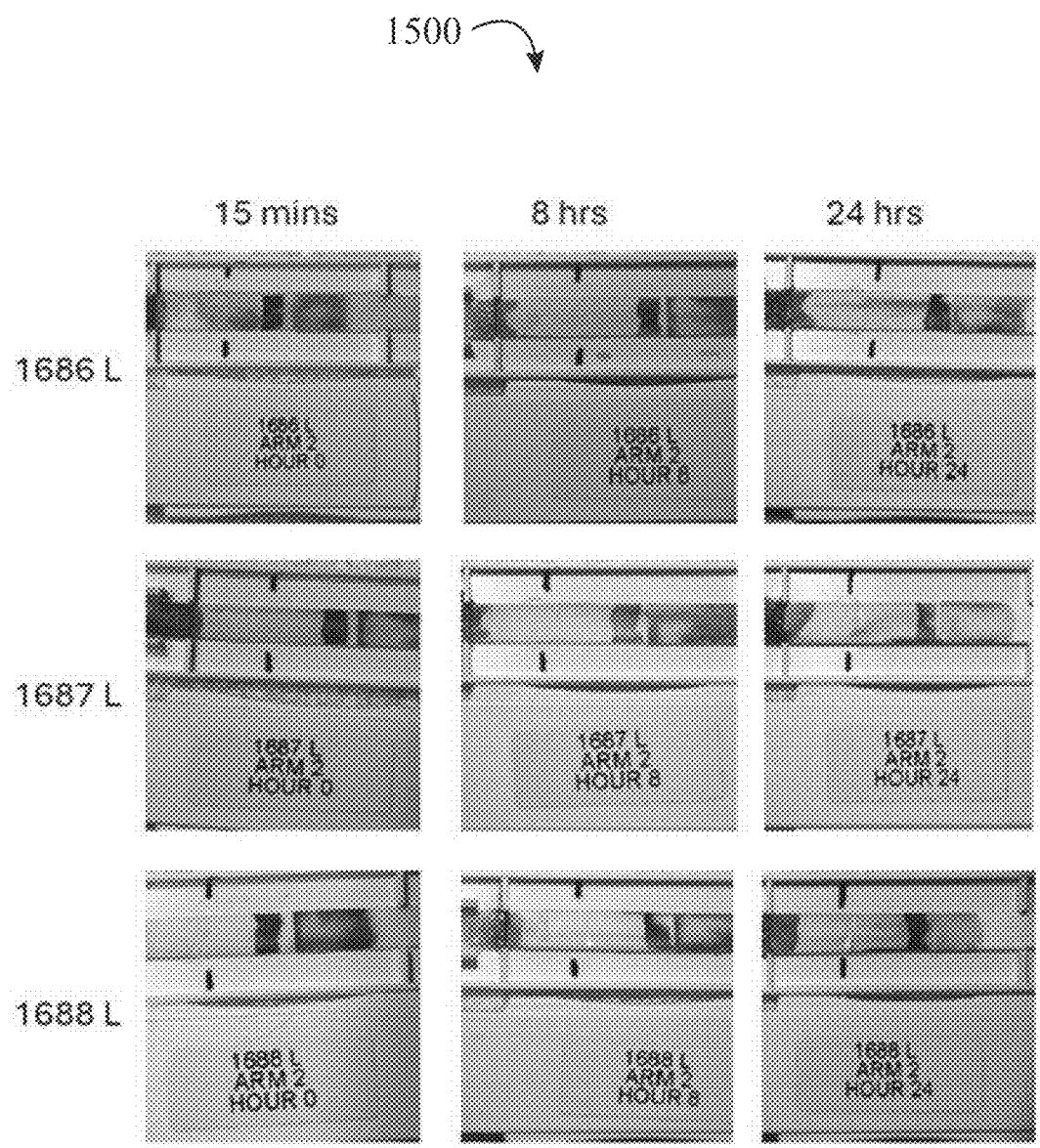
FIG. 15 illustrates results from Arm 2 wounded eyes.

FIG. 14, illustrates results from Arm 1 wounded eyes. The left column numbers refer to specific rabbits and whether the left (wounded) or right (unwounded) eye was sampled. FIG. 15 illustrates results from Arm 2 wounded eyes. The left column numbers refer to specific rabbits and whether the left (wounded) or right (unwounded) eye was sampled. No eyes yielded positive test results following 3 mm surface lacerations in presence (0 of 3 eyes) or absence (0 of 3 eyes) of blood confounder.

Figure 16:
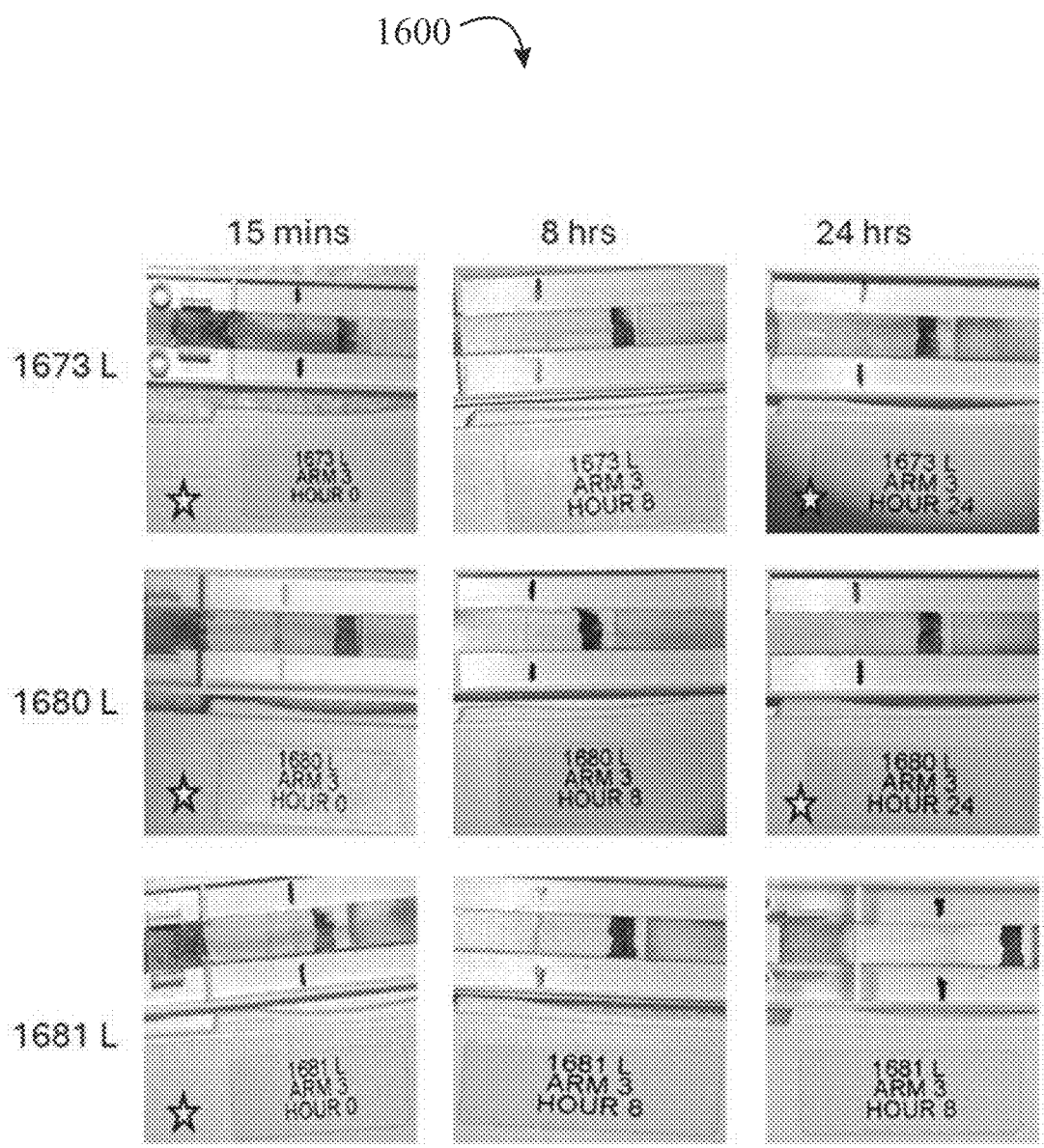
FIG. 16 illustrates results from Arm 3 wounded eyes.
Figure 17:
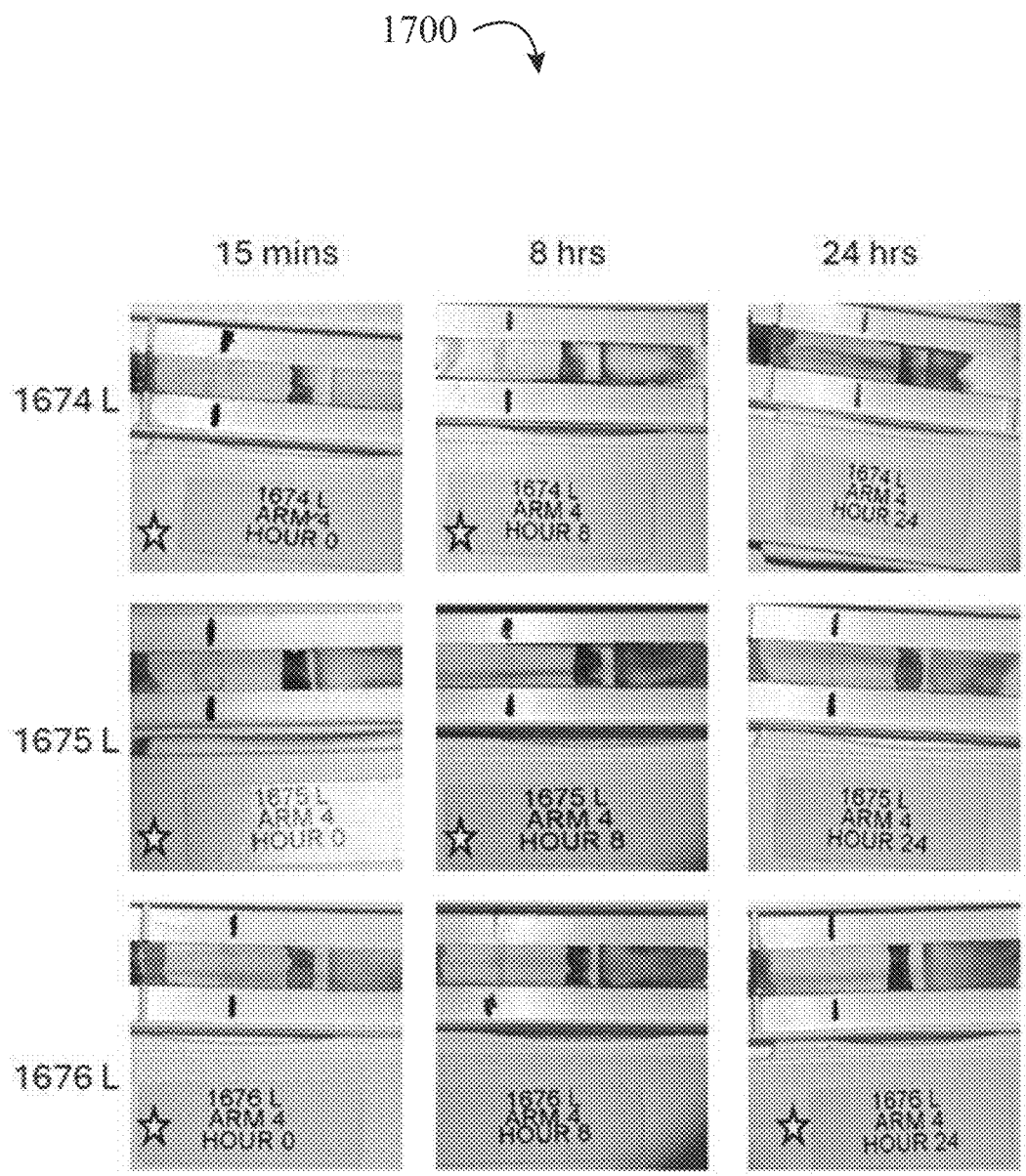
FIG. 17 illustrates results from Arm 4 wounded eyes.

FIG. 16 illustrates results from Arm 3 wounded eyes. The left column numbers refer to specific rabbits and whether the left (wounded) or right (unwounded) eye was sampled. FIG. 17 illustrates results from Arm 4 wounded eyes. The left column numbers refer to specific rabbits and whether the left (wounded) or right (unwounded) eye was sampled. Following full thickness 3 mm lacerations to the AC/limbus in the absence of blood confounder, 2 of 3 eyes at 15 minutes, 2 of 3 eyes at 8 hours, and 1 of 3 eyes at 24 hours, while in the presence of blood confounder 2 of 3 eyes at 15 minutes, 2 of 3 eyes at 8 hours, and 2 of 3 eyes at 24 hours showed a positive test result.

Figure 18:
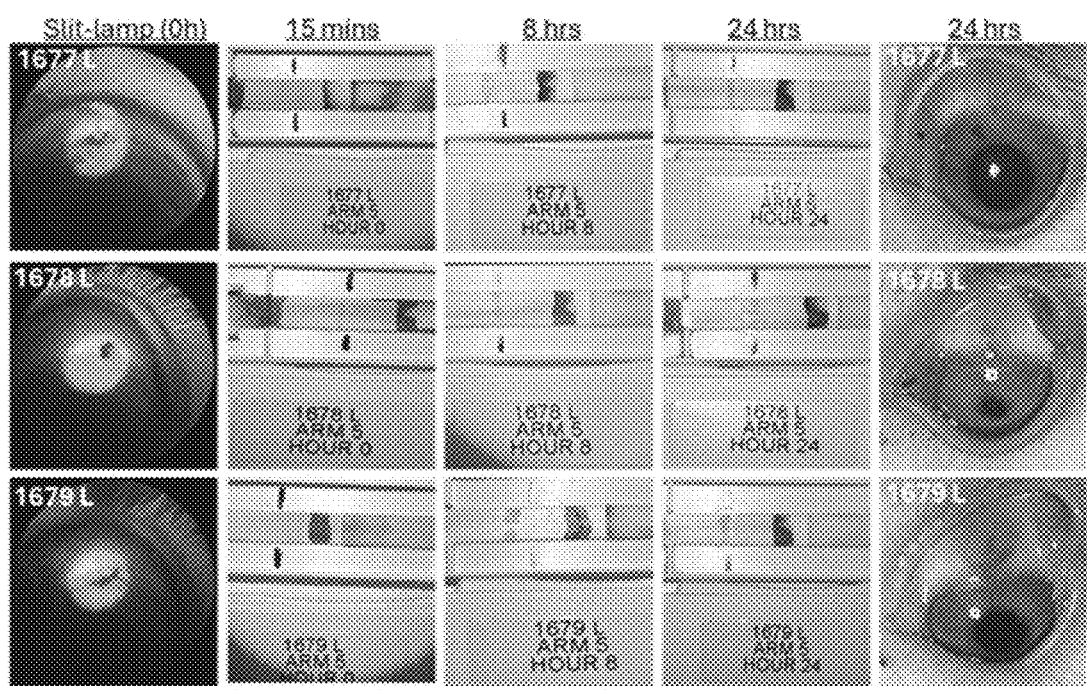
FIG. 18 illustrates results from Arm 5 wounded eyes.
Figure 19:
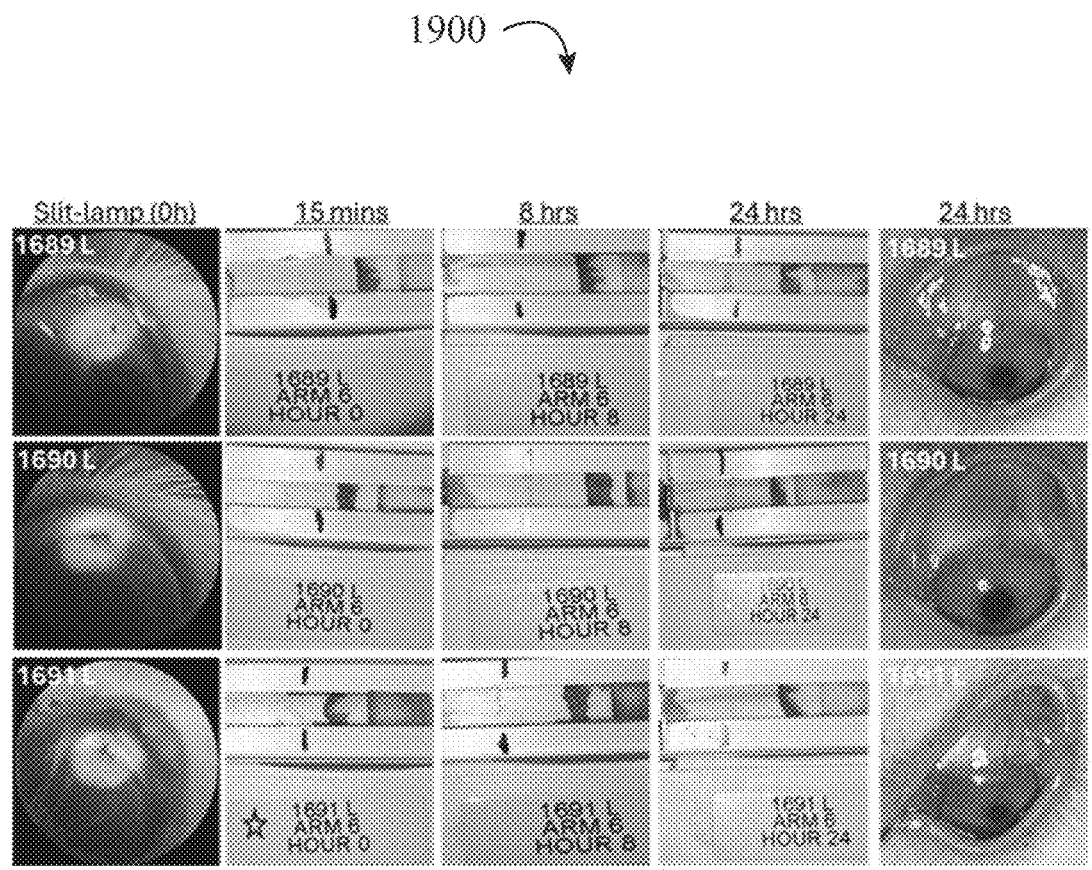
FIG. 19 illustrates results from Arm 6 wounded eyes.

FIG. 18 illustrates results from Arm 5 wounded eyes. The left column numbers refer to specific rabbits and whether the left (wounded) or right (unwounded) eye was sampled. FIG. 19 illustrates results from Arm 6 wounded eyes. The left column numbers refer to specific rabbits and whether the left (wounded) or right (unwounded) eye was sampled. Following full thickness 1 mm lacerations to the AC/limbus in the absence of blood confounder, 0 of 3 eyes, respectively, yielded positive results across all timepoints.

Figure 20:
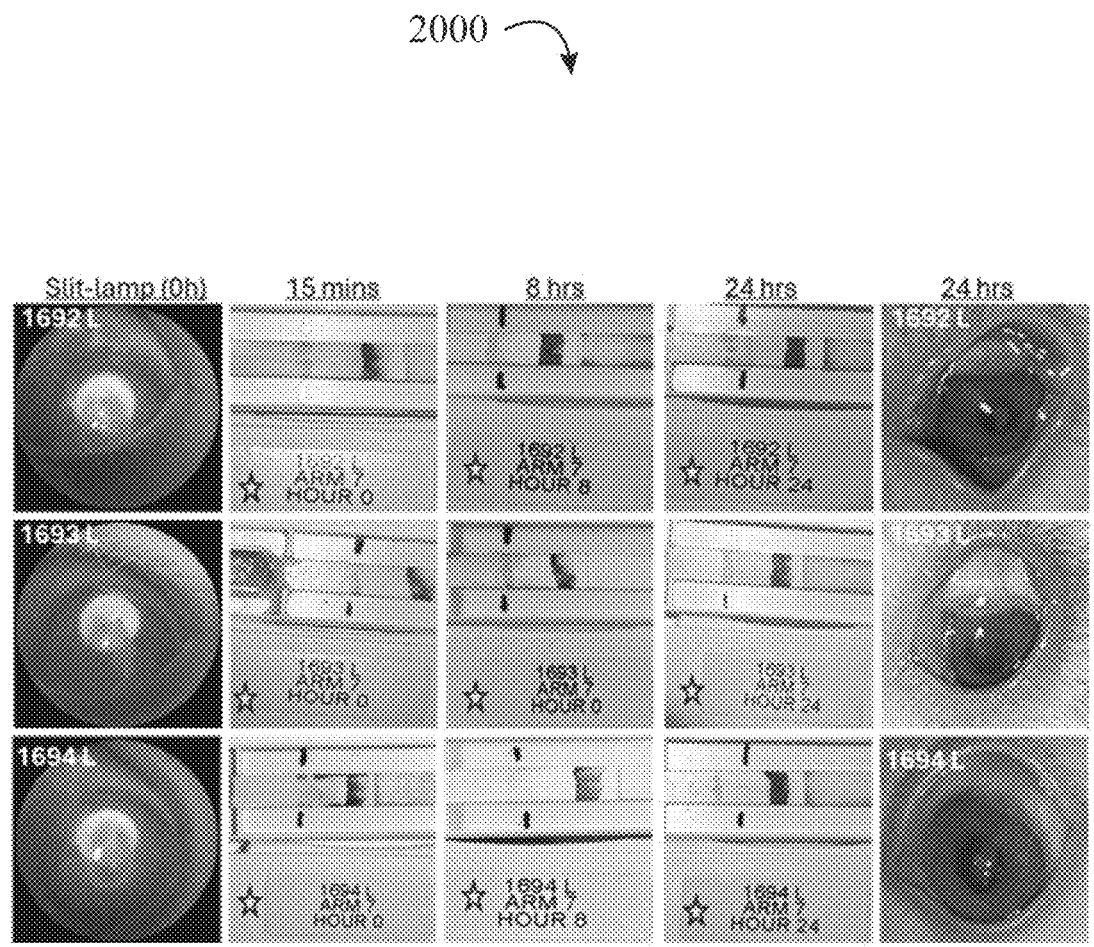
FIG. 20 illustrates results from Arm 7 wounded eyes.
Figure 21:
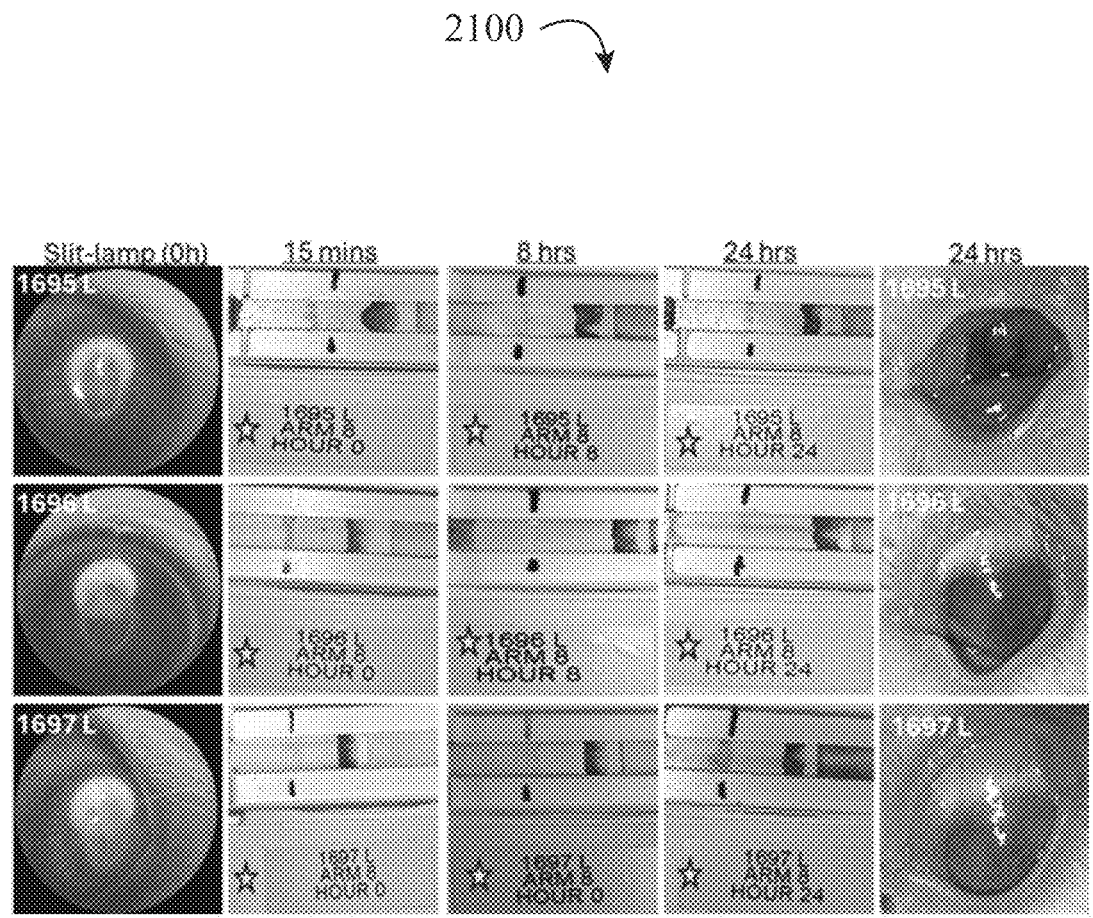
FIG. 21 illustrates results from Arm 8 wounded eyes.

FIG. 20 illustrates results from Arm 7 wounded eyes. The left column numbers refer to specific rabbits and whether the left (wounded) or right (unwounded) eye was sampled. FIG. 21 illustrates results from Arm 8 wounded eyes. The left column numbers refer to specific rabbits and whether the left (wounded) or right (unwounded) eye was sampled. Following full thickness 3 mm lacerations to the PC in the absence of blood confounder, 3 of 3 eyes, respectively, yielded positive results at each of the three timepoints.

Figure 22:
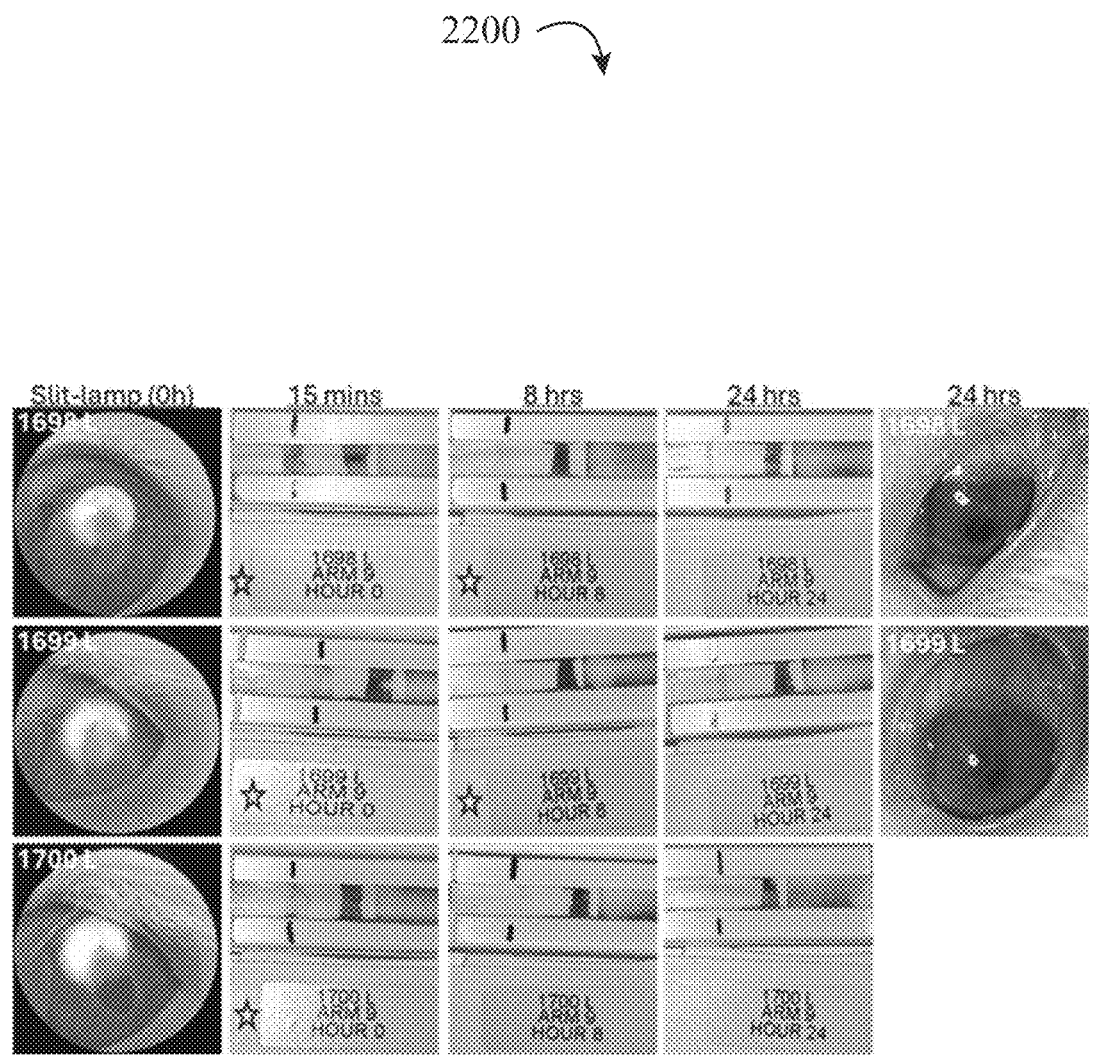
FIG. 22 illustrates results from Arm 9 wounded eyes.
Figure 23:
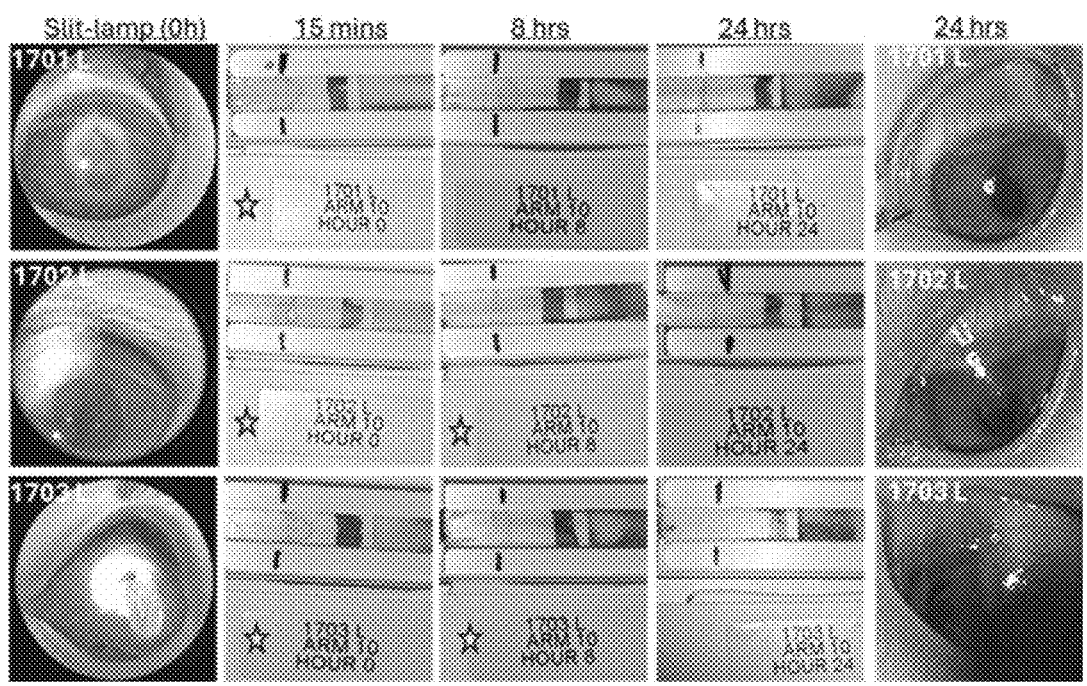
FIG. 23 illustrates results from Arm 10 wounded eyes.

FIG. 22 illustrates results from Arm 9 wounded eyes. The left column numbers refer to specific rabbits and whether the left (wounded) or right (unwounded) eye was sampled. FIG. 23 illustrates results from Arm 10 wounded eyes. The left column numbers refer to specific rabbits and whether the left (wounded) or right (unwounded) eye was sampled. Following full thickness 1 mm puncture to the PC in the absence of blood confounder, 2 of 3 eyes at 15 minutes, 2 of 3 eyes at 8 hours, and 1 of 3 eyes at 24 hours yielded positive results in the presence of blood, and 1 of 3 eyes at 15 minutes, 2 of 3 at 8 hours, and 2 of 3 at 24 hours yielded positive results in the presence of blood.

Full-thickness wounds exposed biomarkers and yielded a positive result. The presence of blood did not impact the results of the readout. Wounds to the peripheral cornea yielded a higher percentage of positive results compared to injuries to the ASC/limbus when comparing across common wound induction methods The results show, so far, that in all cases, when a full-thickness 3 mm laceration was administered, the immediate test 15 minutes post-wounding provided a positive result. This confirms that our device can provide a positive result when a realistic open-globe injury is present. Time points afterwards vary in terms of result, possibly due to resealing or gradual healing of the wound over time, which could also make the device useful for diagnosing whether a wound continues to pose an open-globe risk post-trauma or post-surgery. However, the test lines are, in most cases, relatively faint; therefore, in future iterations of the device, there may be an increase to the concentration of the antibodies in the test lines, and/or increase to the amount of antibody conjugate deposited on the conjugate pad to further increase sensitivity and signal output. The remaining arms of the test are still ongoing.

Sequence Listing Statement

A sequence listing in text format is co-currently submitted and is incorporated by reference as part of this application.

The sequence listing provides the amino acid and nucleic acid sequences for components of the target analyte, target recognition element 108, and test element 116. Specifically, the sequence listing provides: amino acid sequences variations of the target analyte (SEQ ID NO: 1-5); DNA sequence of Target Recognition Element Heavy Chain (SEQ ID NO:6); amino acid sequence of Target Recognition Element Heavy Chain Variable Region Sequence (SEQ ID NO: 7), Target Recognition Element Heavy Chain Variable Region Sequence CDR1 (SEQ ID NO:8), Target Recognition Element Heavy Chain Variable Region Sequence CDR2 (SEQ ID NO:9), Target Recognition Element Heavy Chain Variable Region Sequence CDR3 (SEQ ID NO:10); DNA sequence of Target Recognition Element Light Chain (SEQ ID NO:11); amino acid sequence of Target Recognition Element Light Chain Variable Region Sequence (SEQ ID NO: 12), Target Recognition Element Light Chain Variable Region Sequence CDR1 (SEQ ID NO:13), Target Recognition Element Light Chain Variable Region Sequence CDR2 (SEQ ID NO:14), Target Recognition Element Light Chain Variable Region Sequence CDR3 (SEQ ID NO:15); DNA sequence of Test Element Heavy Chain (SEQ ID NO: 16); amino acid sequence of Test Element Heavy Chain Variable Region Sequence (SEQ ID NO: 17), Test Element Heavy Chain Variable Region Sequence CDR1 (SEQ ID NO:18), Test Element Heavy Chain Variable Region Sequence CDR2 (SEQ ID NO: 19), Test Element Heavy Chain Variable Region Sequence CDR3 (SEQ ID NO:20); DNA sequence of Test Element Light Chain (SEQ ID NO:21); and amino acid sequence of Test Element Light Chain Variable Region Sequence (SEQ ID NO:22), Test Element Light Chain Variable Region Sequence CDR1 (SEQ ID NO: 23), Test Element Light Chain Variable Region Sequence CDR2 (SEQ ID NO:24), Test Element Light Chain Variable Region Sequence CDR3 (SEQ ID NO:25).

The control element 120 antibody may include a commercially available antibody, including Millipore-Sigma part no. M8770 Anti-Mouse IgG1 (heavy chain) from goat as supplied by Sigma-Aldrich, a chemical science company headquartered in St. Louis, MO. Anti-Mouse IgG1 (heavy chain specific) antibody produced in goat has been used in immunohistochemistry and enzyme-linked immunosorbent assay (ELISA).

The present disclosure is not to be limited in terms of the particular embodiments described m this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also understood that this disclosure is not limited to particular compositions, methods, apparatus, and articles, as these may vary. It is also to be understood that the terminology used herein is for the purpose of describing particular embodiments only, and is not intended to be limiting.

Although the present invention has been disclosed in considerable detail with reference to certain preferred versions thereof, other versions are possible. Additionally, the following is a list of embodiments contemplated by the present disclosure:

A1. A fieldable open-globe eye detection system, comprising:
a sampler tool configured to sample a fluid sample from biological fluids proximal to a patient's eye;
a substrate comprising:
  a sample receiver configured to receive the fluid sample from the sampler tool;
  a target recognition element specific to intraocular fluid in fluidic communication with the sample receiver, wherein the target recognition element is configured to bind to a target analyte;
  a signal producing molecule configured to signal the binding of the target recognition element specific to intraocular fluid with the target analyte;
  a flow path from the sample receiver configured to flow the fluid sample, wherein one or both of the target recognition element and the signal producing molecule are downstream of the sample receiver on the flow path;
  a test element downstream from the target recognition element on the flow path and configured to bind, directly or indirectly, to the target analyte; and
  a control element downstream from the target recognition element on the flow path, wherein the control element is configured to bind to the target recognition element;
a casing configured to house the substrate and comprising a display window configured to permit viewing of one or more of the test element and the control element; and
a blood filter configured to filter red blood cells from the fluid sample before the fluid sample reaches the test.

A2. The system of embodiment A1, further comprising at least a light configured to illuminate one or more of the display window and the test element.

A3. The system of embodiment A1, wherein the sampler tool comprises one or more of a soft swab, a syringe, and a pinch grip.

A4. The system of embodiment A1, wherein the sampler tool comprises a soft swab having a shape with a point and the system further comprises a receptor slot configured to receive the soft swab and provide fluidic communication between the soft swab and the sample receiver of the substrate.

A5. The system of embodiment A1, wherein the sampler tool further comprises a syringe containing a buffer, and the sample receiver is further configured to receive the fluid sample within the buffer, directly or indirectly, from the syringe.

A6. The system of embodiment A1, wherein the target analyte comprises at least a portion of α-crystallin A.

A7. The system of embodiment A1, wherein the target analyte is at least 90% identical to SEQ ID NO: 1.

A8. The system of embodiment A1, wherein the target analyte comprises at least six consecutive amino acids of SEQ ID NO: 2.

A9. The system of embodiment A1, wherein the test element comprises an antibody comprising:
a heavy chain variable region CDR1 consisting of SEQ ID NO: 18;
a heavy chain variable region CDR2 consisting of SEQ ID NO: 19; and
a heavy chain variable region CDR3 consisting of SEQ ID NO: 20

A10. The system of embodiment A1, wherein the target recognition element comprises an antibody comprising:
a heavy chain variable region CDR1 consisting of SEQ ID NO: 8;
a heavy chain variable region CDR2 consisting of SEQ ID NO: 9; and
a heavy chain variable region CDR3 consisting of SEQ ID NO: 10.

A11. A method of using a fieldable open-globe eye detection system, comprising:
sampling, using a sampler tool, a fluid sample from biological fluids proximal to a patient's eye;
receiving, using a sample receiver of a substrate, the fluid sample from the sampler tool;
binding, using a target recognition element specific to intraocular fluid in fluidic communication with the sample receiver, to a target analyte;
signaling, using a signal producing molecule of the substrate, the binding of the target recognition element specific to intraocular fluid with the target analyte;
flowing, using a flow path from the sample receiver, the fluid sample, wherein one or both of the target recognition element and the signal producing molecule are downstream of the sample receiver on the flow path;
binding, directly or indirectly, using a test element downstream from the target recognition element on the flow path, to the target analyte;
binding, using a control element downstream from the target recognition element on the flow path, to the target recognition element;
housing, using a casing, the substrate;
permit viewing, using a display window of the casing, of one or more of the test element and the control element; and
filtering, using a blood filter, red blood cells from the fluid sample before the fluid sample reaches the test.

A12. The method of embodiment A11, further comprising illuminating, using at least a light, one or more of the display window and the test element.

A13. The method of embodiment A11, wherein the sampler tool comprises one or more of a soft swab, a syringe, and a pinch grip.

A14. The method of embodiment A11, wherein the sampler tool comprises a soft swab having a shape with a point and the method further comprises:
receiving, using a receptor slot, the soft swab; and
providing, using the receptor slot, fluidic communication between the soft swab and the sample receiver of the substrate.

A15. The method of embodiment A11, wherein the sampler tool further comprises a syringe containing a buffer, and the method further comprises receiving, using the sample receiver the fluid sample within the buffer, directly or indirectly, from the syringe.

A16. The method of embodiment A11, wherein the target analyte comprises at least a portion of α-crystallin A.

A17. The method of embodiment A11, wherein the target analyte is at least 90% identical to SEQ ID NO: 1.

A18. The method of embodiment A11, wherein the target analyte comprises at least six consecutive amino acids of SEQ ID NO: 2.

A19. The method of embodiment A11, wherein the test element comprises an antibody comprising:
a heavy chain variable region CDR1 consisting of SEQ ID NO: 18;
a heavy chain variable region CDR2 consisting of SEQ ID NO: 19; and
a heavy chain variable region CDR3 consisting of SEQ ID NO: 20.

A20. The method of embodiment A11, wherein the target recognition element comprises an antibody comprising:

a heavy chain variable region CDR1 consisting of SEQ ID NO: 8;

a heavy chain variable region CDR2 consisting of SEQ ID NO: 9; and a heavy chain variable region CDR3 consisting of SEQ ID NO: 10.

A21. A kit for treating an open-globe eye injury comprising:

a sample receiver configured to receive a fluid sample from biological fluids proximal to a patient's eye;

a target recognition element specific to intraocular fluid in fluidic communication with the sample receiver, wherein the target recognition element is configured to bind to a target analyte;

a signal producing molecule configured to signal the binding of the target recognition element specific to intraocular fluid with the target analyte; and a colorimetric detection system configured to produce a result associated with open-globe eye injury as a function of the signal producing molecule.

A22. The kit of embodiment A21, wherein the target recognition element comprises one or more of an antibody-binding protein, conjugates, antibody-enzyme label conjugates, antibody-gold nanoparticle conjugates, or any combination thereof.

A23. The kit of embodiment A22, wherein the antibody of the target recognition element comprises:

a heavy chain variable region CDR1 consisting of SEQ ID NO: 8;

a heavy chain variable region CDR2 consisting of SEQ ID NO: 9; and a heavy chain variable region CDR3 consisting of SEQ ID NO: 10.

A24. The kit of embodiment A21, wherein the signal producing molecule comprises a gold nanoparticle.

A25. Th kit of embodiment A21, wherein the sample receiver comprises a sampler tool comprising a swab attached to a handling element.

A26. The kit of embodiment A25, wherein the sampler tool further comprises a running buffer.

A27. The kit of embodiment A21, wherein the colorimetric detection system comprises an enzyme-linked immunosorbent assay (ELISA).

A28. The kit of embodiment A27, wherein the ELISA is in a sandwich assay format.

A29. The kit of embodiment A21, wherein the colorimetric detection system comprises a test element comprising an antibody comprising:

a heavy chain variable region CDR1 consisting of SEQ ID NO: 18;

a heavy chain variable region CDR2 consisting of SEQ ID NO: 19; and a heavy chain variable region CDR3 consisting of SEQ ID NO: 20.

A30. The kit of embodiment A21, further comprising a blood filter configured to filter red blood cells from the fluid sample.

A31. A method for treating an open-globe eye injury in a subject, comprising:

receiving, using a sample receiver, a fluid sample from biological fluids proximal to a patient's eye;

binding, using a target recognition element specific to intraocular fluid in fluidic communication with the sample receiver, to a target analyte;

signaling, using a signal producing molecule, the binding of the target recognition element specific to intraocular fluid with the target analyte;

producing, using a colorimetric detection system, a result associated with open-globe eye injury as a function of the signal producing molecule; and treating the patient for an open-globe eye injury if the result is positive.

A32. The method of embodiment A31, wherein the target recognition element comprises one or more of an antibody-binding protein, conjugates, antibody-enzyme label conjugates, antibody-gold nanoparticle conjugates, or any combination thereof.

A33. The method of embodiment A31, wherein the target analyte is at least 90% identical to SEQ ID NO: 1.

A34. The method of embodiment A31, wherein the target analyte is SEQ ID NO: 1.

A35. The method of embodiment A31, wherein the target analyte comprises at least six consecutive amino acids of SEQ ID NO: 2.

A36. The method of embodiment A31, wherein the target recognition element comprises antibody-binding protein, conjugates, antibody-enzyme label conjugates, antibody-gold nanoparticle conjugates, or any combination thereof.

A37. The method of embodiment A35, wherein the antibody of the target recognition element comprises: a heavy chain variable region CDR1 consisting of SEQ ID NO: 8;

a heavy chain variable region CDR2 consisting of SEQ ID NO: 9; and a heavy chain variable region CDR3 consisting of SEQ ID NO: 10.

A38. The method of embodiment A31, wherein the signal producing molecule comprises a gold nanoparticle.

A39. The method of embodiment A31, wherein the colorimetric detection system comprises a test element comprising an antibody comprising:

a heavy chain variable region CDR1 consisting of SEQ ID NO: 18;

a heavy chain variable region CDR2 consisting of SEQ ID NO: 19; and a heavy chain variable region CDR3 consisting of SEQ ID NO: 20.

A40. The method of embodiment A31, further comprising:

flowing, using a flow path from the sample receiver, the fluid sample; and wherein one or both of the target recognition element and the signal producing molecule are downstream of the sample receiver on the flow path.

A41. A gold nanoparticle (AuNP)-antibody conjugate comprising:

a heavy chain variable region CDR1 consisting of SEQ ID NO: 8;

a heavy chain variable region CDR2 consisting of SEQ ID NO: 9; and a heavy chain variable region CDR3 consisting of SEQ ID NO: 10.

A42. The AuNP-antibody conjugate of embodiment A41, further comprising a light chain variable region CDR1 consisting of SEQ ID NO: 13.

A43. The AuNP-antibody conjugate of embodiment A41, further comprising a light chain variable region CDR2 consisting of SEQ ID NO: 14.

A44. The AuNP-antibody conjugate of embodiment A41, further comprising a light chain variable region CDR3 consisting of SEQ ID NO: 15.

A45. The AuNP-antibody conjugate of embodiment A41, wherein the AuNP-antibody conjugate is configured to specifically bind to an α-Crystallin A protein comprising an amino acid sequence selected from a group consisting of SEQ ID NO: 1-5.

A46. A gold nanoparticle (AuNP)-antibody comprising:
a heavy chain variable region CDR1 consisting of SEQ ID NO: 18;
a heavy chain variable region CDR2 consisting of SEQ ID NO: 19; and
a heavy chain variable region CDR3 consisting of SEQ ID NO: 20.

A47. The AuNP-antibody conjugate of embodiment A46, further comprising a light chain variable region CDR1 consisting of SEQ ID NO: 23.

A48. The AuNP-antibody conjugate of embodiment A46, further comprising a light chain variable region CDR2 consisting of SEQ ID NO: 24.

A49. The AuNP-antibody conjugate of embodiment A46, further comprising a light chain variable region CDR3 consisting of SEQ ID NO: 25.

A50. The AuNP-antibody conjugate of embodiment A46, wherein the AuNP-antibody conjugate is configured to specifically bind to an α-Crystallin A protein comprising an amino acid sequence selected from a group consisting of SEQ ID NO: 1-5.

A51. Any of the above embodiments A1-A50 further comprising an antibody comprising:
a light chain variable region CDR1 consisting of SEQ ID NO: 23;
a light chain variable region CDR2 consisting of SEQ ID NO: 24; and
a light chain variable region CDR3 consisting of SEQ ID NO: 25.

SEQUENCE LISTING

```
Sequence total quantity: 25
SEQ ID NO: 1            moltype = AA  length = 173
FEATURE                 Location/Qualifiers
source                  1..173
                        mol_type = protein
                        organism = Homo sapiens
SEQUENCE: 1
MDVTIQHPWF KRTLGPFYPS RLFDQFFGEG LFEYDLLPFL SSTISPYYRQ SLFRTVLDSG  60
ISEVRSDRDK FVIFLDVKHF SPEDLTVKVQ DDFVEIHGKH NERQDDHGYI SREFHRRYRL 120
PSNVDQSALS CSLSADGMLT FCGPKIQTGL DATHAERAIP VSREEKPTSA PSS        173

SEQ ID NO: 2            moltype = AA  length = 39
FEATURE                 Location/Qualifiers
source                  1..39
                        mol_type = protein
                        organism = Homo sapiens
SEQUENCE: 2
SADGMLTFSG PKIQTGLDAT HAERAIPVSR EEKPTSAPS                          39

SEQ ID NO: 3            moltype = AA  length = 7
FEATURE                 Location/Qualifiers
source                  1..7
                        mol_type = protein
                        organism = Homo sapiens
SEQUENCE: 3
PTSAPSS                                                              7

SEQ ID NO: 4            moltype = AA  length = 10
FEATURE                 Location/Qualifiers
source                  1..10
                        mol_type = protein
                        organism = Homo sapiens
SEQUENCE: 4
MLTFCGPKIQ                                                          10

SEQ ID NO: 5            moltype = AA  length = 10
FEATURE                 Location/Qualifiers
source                  1..10
                        mol_type = protein
                        organism = Homo sapiens
SEQUENCE: 5
MLTFSGPKIQ                                                          10

SEQ ID NO: 6            moltype = DNA  length = 1308
FEATURE                 Location/Qualifiers
source                  1..1308
                        mol_type = genomic DNA
                        organism = Oryctolagus cuniculus
SEQUENCE: 6
gaggtgaagc tgcaggagtc aggacctagc ctggtgaaac cttctcagac tctgtccctc  60
acctgttctg tcactggcga ctccatcacc agtggttact ggaactggat ccggaaattc 120
ccagggaata aacttgagta tatggggtat ataagttaca gtggtagcac ttacttcaat 180
ccatctctca aaagtcgaat ctccatcact cgagacacat ccaagaacca gtactacctg 240
cagttgaatt ctgtgactac tgaggacaca gccacatatt actgtgtcaac cgggtttgct 300
tactgggggcc aagggactct ggtcactgtc tctgcagcca aaacgacacc cccatctgtc 360
tatccactgg ccctgtgat gctgcccaa actaactcca tggtgaccct gggatgcctg 420
gtcaagggct atttcccctga ccagtgaca gtgacctgga actctggatc cctgtccagc 480
```

-continued

```
ggtgtgcaca ccttcccagc tgtcctgcag tctgacctct acactctgag cagctcagtg    540
actgtcccct ccagcacctg gcccagccag accgtcacct gcaacgttgc ccacccggcc    600
agcagcacca aggtggacaa gaaaattgtg cccagggatt gtggttgtaa gccttgcata    660
tgtacagtcc cagaagtatc atctgtcttc atcttccccc caaagcccaa ggatgtgctc    720
accattactc tgactcctaa ggtcacgtgt gttgtggtag acatcagcaa ggatgatcct    780
gaggtccagt tcagctggtt tgtagatgat gtggaggtgc acacagctca gacgcaaccc    840
cgggaggagc agttcaacag cacttccgc tcagtcagtg aacttcccat catgcaccag    900
gactggctca atggcaagga gttcaaatgc agggtcaaca gtgcagcttt ccctgccccc    960
atcgagaaaa ccatctccaa aaccaaaggc agaccaaagg ctccacaggt gtacaccatt   1020
ccacctccca aggagcagat ggccaaggat aaagtcagtc tgacctgcat gataacagac   1080
ttcttccctg aagacattac tgtggagtgg cagtggaatg ggcagccagc ggagaactac   1140
aagaacactc agcccatcat ggacacagat ggctcttact tcgtctacag caagctcaat   1200
gtgcagaaga gcaactggga ggcaggaaat actttcacct gctctgtgtt gcatgagggc   1260
ctgcacaacc accatactga gaagagcctc tcccactctc tggtaaa             1308

SEQ ID NO: 7                moltype = AA   length = 436
FEATURE                     Location/Qualifiers
source                      1..436
                            mol_type = protein
                            organism = Oryctolagus cuniculus
SEQUENCE: 7
EVKLQESGPS LVKPSQTLSL TCSVTGDSIT SGYWNWIRKF PGNKLEYMGY ISYSGSTYFN     60
PSLKSRISIT RDTSKNQYYL QLNSVTTEDT ATYYCSTGFA YWGQGTLVTV SAAKTTPPSV    120
YPLAPGSAAQ TNSMVTLGCL VKGYFPEPVT VTWNSGSLSS GVHTFPAVLQ SDLYTLSSSV    180
TVPSSTWPSQ TVTCNVAHPA SSTKVDKKIV PRDCGCKPCI CTVPEVSSVF IFPPKPKDVL    240
TITLTPKVTC VVVDISKDDP EVQFSWFVDD VEVHTAQTQP REEQFNSTFR SVSELPIMHQ    300
DWLNGKEFKC RVNSAAFPAP IEKTISKTKG RPKAPQVYTI PPPKEQMAKD KVSLTCMITD    360
FFPEDITVEW QWNGQPAENY KNTQPIMDTD GSYFVYSKLN VQKSNWEAGN TFTCSVLHEG    420
LHNHHTEKSL SHSPGK                                                   436

SEQ ID NO: 8                moltype = AA   length = 8
FEATURE                     Location/Qualifiers
source                      1..8
                            mol_type = protein
                            organism = Oryctolagus cuniculus
SEQUENCE: 8
GDSITSGY                                                              8

SEQ ID NO: 9                moltype = AA   length = 7
FEATURE                     Location/Qualifiers
source                      1..7
                            mol_type = protein
                            organism = Oryctolagus cuniculus
SEQUENCE: 9
ISYSGST                                                               7

SEQ ID NO: 10               moltype = AA   length = 6
FEATURE                     Location/Qualifiers
source                      1..6
                            mol_type = protein
                            organism = Oryctolagus cuniculus
SEQUENCE: 10
STGFAY                                                                6

SEQ ID NO: 11               moltype = DNA   length = 660
FEATURE                     Location/Qualifiers
source                      1..660
                            mol_type = genomic DNA
                            organism = Oryctolagus cuniculus
SEQUENCE: 11
gacattgtga tgtcacagtc tccatcctcc ctagctgtgt cagttggaga gaaggttatt     60
atgagatgca actccagtca gagccttta tatagtggca atcgcgagaa ctacttggcc    120
tggtaccagc agaaaccagg gcagtctcct aacctgctga tttattgggc atccagaagg    180
gcatctgggg tccctgatcg cttcgcaggc ggtggatctg gacagactt cactctcacc    240
atcagcagtg tgaaggctga agacctggca gtttattact gtcagcatta ttataactat    300
cctctcacgt tcggtgctgg gaccaggctg gagctgaaac gggctgatgc tgcaccaact    360
gtatccatct tcccaccatc cagtgagcag ttaacatctg gaggtgcctc agtcgtgtgc    420
ttcttgaaca acttcacccc cagagacatc aatgtcaagt ggaagattga tggcagtgaa    480
cgacaaaatg gtgtcctgaa cagttggact gatcaggaca gcaaagacag cacctacagc    540
atgagcagca ccctcacatt gaccaaggac gagtatgaac acataacag ctatacctgt    600
gaggccactc acaagacatc aacttccaccc attgtcaaga gcttcaacag gaatgagtgt    660

SEQ ID NO: 12               moltype = AA   length = 220
FEATURE                     Location/Qualifiers
source                      1..220
                            mol_type = protein
                            organism = Oryctolagus cuniculus
SEQUENCE: 12
DIVMSQSPSS LAVSVGEKVI MRCNSSQSLL YSGNRENYLA WYQQKPGQSP NLLIYWASRR     60
```

```
ASGVPDRFAG GGSGTDFTLT ISSVKAEDLA VYYCQHYYNY PLTFGAGTRL ELKRADAAPT    120
VSIFPPSSEQ LTSGGASVVC FLNNFYPRDI NVKWKIDGSE RQNGVLNSWT DQDSKDSTYS    180
MSSTLTLTKD EYERHNSYTC EATHKTSTSP IVKSFNRNEC                          220

SEQ ID NO: 13           moltype = AA  length = 12
FEATURE                 Location/Qualifiers
source                  1..12
                        mol_type = protein
                        organism = Oryctolagus cuniculus
SEQUENCE: 13
QSLLYSGNRE NY                                                         12

SEQ ID NO: 14           moltype =     length =
SEQUENCE: 14
000

SEQ ID NO: 15           moltype = AA  length = 9
FEATURE                 Location/Qualifiers
source                  1..9
                        mol_type = protein
                        organism = Oryctolagus cuniculus
SEQUENCE: 15
QHYYNYPLT                                                              9

SEQ ID NO: 16           moltype = DNA  length = 1338
FEATURE                 Location/Qualifiers
source                  1..1338
                        mol_type = genomic DNA
                        organism = Oryctolagus cuniculus
SEQUENCE: 16
gaggtgaagc tgcaggagtc aggacctagc ctggtgagac ccggagcttc cgtgaagatg     60
tcctgtaagg cctccggcta cacctttaca tcctacaaca tgcactgggt gaagcagacc    120
cccagacagg gcctggagtg gatcggcgcc atctacctg caacggcga cacaagctac      180
aaccagaagt tcaagggcaa ggccacactg accgtgaca agtccagctc cacagctac      240
atgcagctga gcagcctgac aagcgaggat agcgccgtgt acttttgcgc cagagtggtg    300
tactactcca attcctactg gtacttcgat gtgtggggca caggcaccac cgtgacagtg    360
tccgccgcca aaacgacacc cccatctgtc tatccactgg cccctggatc tgctgcccaa    420
actaactcca tggtgaccct gggatgcctg gtcaagggc atttccctga ccagtgaca     480
gtgacctgga actctggatc cctgtccagc ggtgtgcaca ccttcccagc tgtcctgcag    540
tctgacctct acactctgag cagctcagtg actgtcccct ccagcacctg cccagccag    600
accgtcacct gcaacgttgc ccaccccggcc agcagcacca aggtgacaa gaaaattgtg    660
cccagggatt gtggttgtaa gccttgcata tgtacagtcc cagaagtatc atctgtcttc    720
atcttccccc caaagcccaa ggatgtgctc accattactc ttcctcctaa ggtcacgtgt    780
gttgtggtag acatcagcaa ggatgatccc gaggtccagt tcagctggtt tgtagatgat    840
gtggaggtgc acacagctca gacgcaaccc cggaggagc agttcaacag cacttttccgc    900
tcagtcagtg aacttcccat catgcaccag gactggctca atggcaagga gttcaaatgc    960
agggtcaaca gtgcagcttt ccctgccccc atcgagaaaa ccatctccaa aaccaaaggc   1020
agaccaaagg ctccacaggt gtacaccatt ccacctccca aggagcagat ggccaaggat   1080
aaagtcagtc tgacctgcat gataacagac ttcttccctg aagacattac tgtggagtgg   1140
cagtggaatg ggcagccagc ggagaactac aagaacactc agcccatcat ggacacagat   1200
ggctcttact tcgtctacag caagctcaat gtgcagaaga caactggga ggcaggaaat    1260
actttcacct gctccgtgtt gcatgagggc ctgcacaacc accatactga aaagagcctc   1320
tcccactctc ctggtaaa                                                 1338

SEQ ID NO: 17           moltype = AA  length = 446
FEATURE                 Location/Qualifiers
source                  1..446
                        mol_type = protein
                        organism = Oryctolagus cuniculus
SEQUENCE: 17
EVKLQESGPS LVRPGASVKM SCKASGYTFT SYNMHWVKQT PRQGLEWIGA IYPGNGDTSY     60
NQKFKGKATL TVDKSSSTAY MQLSSLTSED SAVYFCARVV YYSNSYWYFD VWGTGTTVTV    120
SAAKTTPPSV YPLAPGSAAQ TNSMVTLGCL VKGYFPEPVT VTWNSGSLSS GVHTFPAVLQ    180
SDLYTLSSSV TVPSSTWPSQ TVTCNVAHPA SSTKVDKKIV PRDCGCKPCI CTVPEVSSVF    240
IPPPKPKDVL TITLTPKVTC VVVDISKDDP EVQFSWFVDD VEVHTAQTQP REEQFNSTFR    300
SVSELPIMHQ DWLNGKEFKC RVNSAAFPAP IEKTISKTKG RPKAPQVYTI PPPKEQMAKD    360
KVSLTCMITD FFPEDITVEW QWNGQPAENY KNTQPIMDTD GSYFVYSKLN VQKSNWEAGN    420
TFTCSVLHEG LHNHHTEKSL SHSPGK                                         446

SEQ ID NO: 18           moltype = AA  length = 8
FEATURE                 Location/Qualifiers
source                  1..8
                        mol_type = protein
                        organism = Oryctolagus cuniculus
SEQUENCE: 18
GYTFTSYN                                                               8

SEQ ID NO: 19           moltype = AA  length = 8
FEATURE                 Location/Qualifiers
```

```
source              1..8
                    mol_type = protein
                    organism = Oryctolagus cuniculus
SEQUENCE: 19
IYPGNGDT                                                                    8

SEQ ID NO: 20       moltype = AA  length = 15
FEATURE             Location/Qualifiers
source              1..15
                    mol_type = protein
                    organism = Oryctolagus cuniculus
SEQUENCE: 20
ARVVYYSNSY WYFDV                                                           15

SEQ ID NO: 21       moltype = DNA  length = 660
FEATURE             Location/Qualifiers
source              1..660
                    mol_type = genomic DNA
                    organism = Oryctolagus cuniculus
SEQUENCE: 21
gacattgtga tgtcacagtc tccatcctcc ctagctgtgt cagttggaga gaaggttatt           60
atgagatgca actccagtca gagcctttta tatagtggca atgagagaa ctacttggcc          120
tggtaccagc agaaaccagg gcagtctcct aatctgctga tttattgggc atccagaagg         180
gcatctgggg tccctgatcg cttcgcaggc agtggatctg gacagactt cactctcacc          240
atcagcagtg tgaaggctga agacctggca gtttattact gtcagcatta ttataactat         300
cctctcacgt tcggtgctgg gaccaggctg gagctgatgc tgtcaccaact                    360
gtatccatct tcccaccatc cagtgagcag ttaacatctg gaggtgcctc agtcgtgtgc          420
ttcttgaaca acttctaccc cagagacatc aatgtcaagt ggaagattga tggcagtgaa          480
cgacaaaatg gtgtcctgaa cagttggact gatcaggaca gcaaagacag cacctacagc          540
atgagcagca ccctcacatt gaccaaggac gagtatgaac gacataacag ctatacctgt          600
gaggccactc acaagacatc aacttcaccc attgtcaaga gcttcaacag gaatgagtgt          660

SEQ ID NO: 22       moltype = AA  length = 220
FEATURE             Location/Qualifiers
source              1..220
                    mol_type = protein
                    organism = Oryctolagus cuniculus
SEQUENCE: 22
DIVMSQSPSS LAVSVGEKVI MRCNSSQSLL YSGNRENYLA WYQQKPGQSP NLLIYWASRR           60
ASGVPDRFAG SGSGTDFTLT ISSVKAEDLA VYYCQHYYNY PLTFGAGTRL ELKRADAAPT          120
VSIFPPSSEQ LTSGGASVVC FLNNFYPRDI NVKWKIDGSE RQNGVLNSWT DQDSKDSTYS          180
MSSTLTLTKD EYERHNSYTC EATHKTSTSP IVKSFNRNEC                                220

SEQ ID NO: 23       moltype = AA  length = 12
FEATURE             Location/Qualifiers
source              1..12
                    mol_type = protein
                    organism = Oryctolagus cuniculus
SEQUENCE: 23
QSLLYSGNRE NY                                                              12

SEQ ID NO: 24       moltype =   length =
SEQUENCE: 24
000

SEQ ID NO: 25       moltype = AA  length = 9
FEATURE             Location/Qualifiers
source              1..9
                    mol_type = protein
                    organism = Oryctolagus cuniculus
SEQUENCE: 25
QHYYNYPLT                                                                   9
```

What is claimed is:

1. A lateral flow device substrate comprising:
a. an assay strip substrate comprising a sample receiver pad capable to receive an ocular fluid sample;
b. a conjugate pad in fluidic communication with the sample receiver pad and positioned downstream the sample pad on the substrate, wherein the conjugate pad comprises a first antibody; and
c. a test pad positioned downstream of the conjugate pad wherein the test pad comprises a test antibody immobilized thereof to form a test line,
wherein the first and test antibody are selected from a group consisting of (1) an antibody comprising a heavy chain variable region CDR1 consisting of SEQ ID NO: 8; a heavy chain variable region CDR2 consisting of SEQ ID NO: 9; and a heavy chain variable region CDR3 consisting of SEQ ID NO: 10 and a light chain variable region CDR1 consisting of SEQ ID NO: 13; a light chain variable region CDR2 consisting of amino acids sequence WAS; and a light chain variable region CDR3 consisting of SEQ ID NO: 15; and (2) an antibody comprising a heavy chain variable region CDR1 consisting of SEQ ID NO: 18; a heavy chain variable region CDR2 consisting of SEQ ID NO: 19; a heavy chain variable region CDR3 consisting of SEQ ID NO: 20 and a light chain variable region CDR1 consisting of SEQ ID NO: 23; a light chain variable region CDR2 consisting of amino acids sequence WAS; and a light chain variable region CDR3 consisting of SEQ ID NO: 25, wherein the first antibody is conjugated to a signal producing label, and wherein each of the first and test antibody specifically bind human and rabbit α-crystallin A protein.

2. The device of claim 1 further comprising: a blood filter capable to retain red blood cells from the ocular fluid and to allow soluble proteins in the ocular fluid to flow into the conjugate pad, wherein the blood filter is positioned on top of the conjugate pad or incorporated in the conjugate pad.

3. The device of claim 1, wherein the test pad further comprises a control element immobilized thereof to form a control line, wherein the control element is capable to bind the first antibody.

4. The device of claim 1, wherein the first antibody comprises the heavy chain variable region CDR1 consisting of SEQ ID NO: 8; the heavy chain variable region CDR2 consisting of SEQ ID NO: 9; and the heavy chain variable region CDR3 consisting of SEQ ID NO: 10 and the light chain variable region CDR1 consisting of SEQ ID NO: 13; the light chain variable region CDR2 consisting of amino acids sequence WAS; and the light chain variable region CDR3 consisting of SEQ ID NO: 15 and wherein the test antibody comprises the heavy chain variable region CDR1 consisting of SEQ ID NO: 18; the heavy chain variable region CDR2 consisting of SEQ ID NO: 19; the heavy chain variable region CDR3 consisting of SEQ ID NO: 20 and the light chain variable region CDR1 consisting of SEQ ID NO: 23; the light chain variable region CDR2 consisting of amino acids sequence WAS; and the light chain variable region CDR3 consisting of SEQ ID NO: 25.

5. The device of claim 1, wherein the first antibody comprises VL sequence of SEQ ID NO: 12 and VH sequence of SEQ ID NO:7 and the test antibody comprises the VL sequence of SEQ ID NO:22 and VH sequence of SEQ ID NO:17.

6. A lateral flow assay method for detecting α-crystallin A protein in a sample comprising:

performing an assay with the lateral flow device of claim 1, comprising:

obtaining an ocular fluid sample from a human or rabbit subject, placing the ocular fluid sample on the sample receiver pad; and detecting binding between α-crystallin A, the first and test antibody by detecting the signal produced by the label at the test line, wherein the presence of signal is indicative of presence of the α-crystallin A in the ocular fluid sample.

7. The method of claim 6, wherein the first antibody comprises VL sequence of SEQ ID NO: 12 and VH sequence of SEQ ID NO:7 and the test antibody comprises the VL sequence of SEQ ID NO:22 and the VH sequence of SEQ ID NO:17.

8. The method of claim 6, wherein the first antibody comprises the heavy chain variable region CDR1 consisting of SEQ ID NO: 8; the heavy chain variable region CDR2 consisting of SEQ ID NO: 9; and the heavy chain variable region CDR3 consisting of SEQ ID NO: 10 and the light chain variable region CDR1 consisting of SEQ ID NO: 13; the light chain variable region CDR2 consisting of amino acids sequence WAS; and the light chain variable region CDR3 consisting of SEQ ID NO: 15 and wherein the test antibody comprises the heavy chain variable region CDR1 consisting of SEQ ID NO: 18; the heavy chain variable region CDR2 consisting of SEQ ID NO: 19; the heavy chain variable region CDR3 consisting of SEQ ID NO: 20 and the light chain variable region CDR1 consisting of SEQ ID NO: 23; the light chain variable region CDR2 consisting of amino acids sequence WAS; and the light chain variable region CDR3 consisting of SEQ ID NO: 25.

* * * * *